US009410832B2

(12) United States Patent
Richter et al.

(10) Patent No.: US 9,410,832 B2
(45) Date of Patent: Aug. 9, 2016

(54) MICROFLUIDIC DEVICE, MICROFLUIDIC DOSING SYSTEM AND METHOD FOR MICROFLUIDIC FLOW MEASUREMENT AND DOSING

(71) Applicant: Fraunhofer-Gesellschaft zur Foerderung der angewandten Forschung e.V., Munich (DE)

(72) Inventors: Martin Richter, Munich (DE); Sebastian Kibler, Munich (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 359 days.

(21) Appl. No.: 13/788,110

(22) Filed: Mar. 7, 2013

(65) Prior Publication Data

US 2013/0183209 A1 Jul. 18, 2013

Related U.S. Application Data

(63) Continuation of application No. PCT/EP2010/063255, filed on Sep. 9, 2010.

(51) Int. Cl.
| | |
|---|---|
| *G01F 1/58* | (2006.01) |
| *G01F 1/00* | (2006.01) |
| *F15C 1/04* | (2006.01) |
| *A61M 5/168* | (2006.01) |
| *C40B 60/14* | (2006.01) |
| *C40B 50/08* | (2006.01) |
| *B01F 13/00* | (2006.01) |
| *B01L 3/00* | (2006.01) |
| *A61M 5/142* | (2006.01) |

(52) U.S. Cl.
CPC ............ *G01F 1/588* (2013.01); *A61M 5/16804* (2013.01); *A61M 5/16827* (2013.01); *A61M 5/16877* (2013.01); *A61M 5/16886* (2013.01); *B01L 3/502784* (2013.01); *A61M 5/14276* (2013.01); *B01F 13/0071* (2013.01); *B01L 3/502761* (2013.01); *B01L 3/502776* (2013.01); *B01L 2200/0605* (2013.01); *B01L 2200/0673* (2013.01); *B01L 2200/14* (2013.01); *B01L 2300/0627* (2013.01); *B01L 2300/0681* (2013.01); *B01L 2300/0867* (2013.01);
(Continued)

(58) Field of Classification Search
None
See application file for complete search history.

(56) References Cited

U.S. PATENT DOCUMENTS

| | | | | |
|---|---|---|---|---|
| 2002/0143437 A1* | 10/2002 | Handique et al. | ............. | 700/266 |
| 2003/0138359 A1* | 7/2003 | Chow et al. | ................... | 422/101 |

(Continued)

FOREIGN PATENT DOCUMENTS

| | | |
|---|---|---|
| JP | 2004-270537 A | 9/2004 |
| WO | 2005/118138 A1 | 12/2005 |

OTHER PUBLICATIONS

Official Communication issued in International Patent Application No. PCT/EP2010/063255, mailed on Jun. 7, 2011.

*Primary Examiner* — Jennifer Wecker
(74) *Attorney, Agent, or Firm* — Keating & Bennett, LLP

(57) ABSTRACT

A microfluidic device for detecting a flow parameter, includes a channel configured within a base body, the channel including a first inlet for feeding a first fluid and a second inlet for feeding a second fluid so as to form a fluid stream having the first and second fluids within the channel, and further including an output for providing the fluid stream on the output side, a first feeder including a micropump associated with the first inlet for selectively feeding the first fluid to the channel, a second feeder associated with the second inlet for feeding the second fluid to the channel; and a detector for detecting, on the basis of a different physical property of the first fluid and the second fluid within the channel, a measurement value dependent on a current flow parameter of the first or second fluid.

18 Claims, 11 Drawing Sheets

(52) U.S. Cl.
CPC .. *B01L2300/0877* (2013.01); *B01L 2300/0887* (2013.01)

(56) References Cited

U.S. PATENT DOCUMENTS

| | | | |
|---|---|---|---|
| 2004/0115068 A1* | 6/2004 | Hansen et al. | 417/379 |
| 2004/0166028 A1* | 8/2004 | Husar et al. | 422/100 |
| 2006/0090576 A1* | 5/2006 | Sander | 73/864.01 |
| 2006/0096923 A1 | 5/2006 | Wagler et al. | |
| 2007/0138076 A1* | 6/2007 | Daridon et al. | 210/198.2 |
| 2008/0131323 A1* | 6/2008 | Kuczenski et al. | 422/82.13 |
| 2009/0019924 A1* | 1/2009 | Nguyen et al. | 73/64.52 |
| 2009/0023223 A1* | 1/2009 | Eastwood et al. | 436/172 |
| 2010/0000620 A1* | 1/2010 | Fouillet et al. | 137/827 |
| 2010/0029512 A1* | 2/2010 | Davies et al. | 506/27 |
| 2010/0102463 A1* | 4/2010 | Arnet | 264/1.1 |
| 2011/0124113 A1* | 5/2011 | Azad et al. | 436/139 |
| 2011/0239757 A1* | 10/2011 | Camenisch et al. | 73/304 |

\* cited by examiner

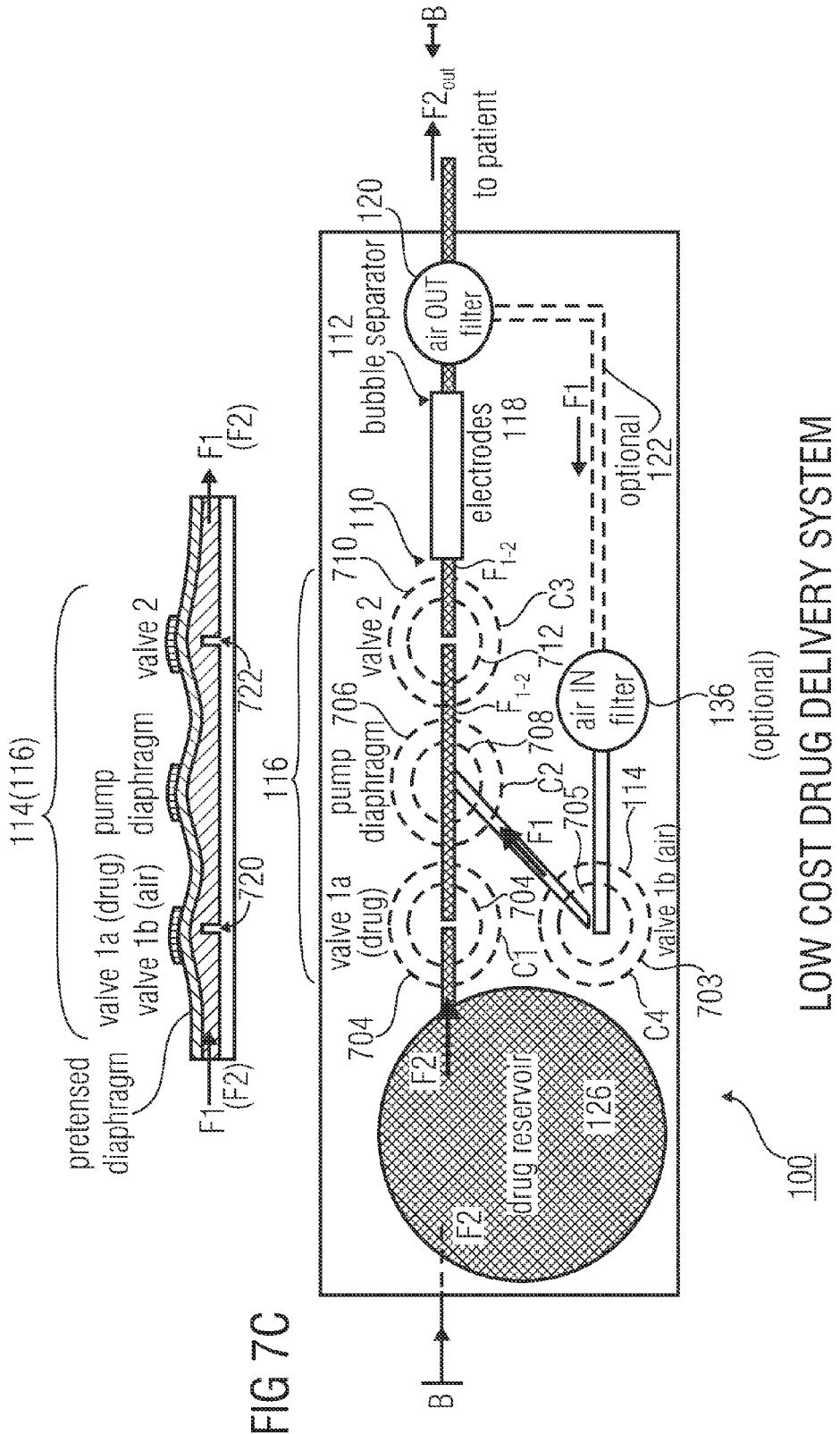

MICROFLUIDIC DEVICE, MICROFLUIDIC DOSING SYSTEM AND METHOD FOR MICROFLUIDIC FLOW MEASUREMENT AND DOSING

CROSS-REFERENCE TO RELATED APPLICATIONS

This application is a continuation of copending International Application No. PCT/EP2010/063255, filed Sep. 9, 2010, which is incorporated herein by reference in its entirety.

BACKGROUND OF THE INVENTION

The present invention relates to a microfluidic device for detecting a flow parameter, a microfluidic dosing system, a method for detecting a flow parameter of a fluid stream within a channel and to a method for microfluidically dosing a fluid. In particular, the present invention relates to a microdosing concept for dosing minute quantities of fluids, such as, for example, quantities of a liquid or gas, within a fluid channel.

In the field of medical technology, but also in other fields of technology, there is demand for dosing minute quantities or volumes of fluids (exemplarily in the range of nanoliters to microliters) with sufficient precision, and additionally also for being able to monitor this precise dosing process in terms of measuring technology.

Micromembrane or microdiaphragm pumps, for example, are employed in the field of medical technology for dosing carrier liquids or drugs, such as, for example, for infusions. At present, micromembrane pumps, the functional principle of which is based on deflecting a membrane or diaphragm, are generally not able to achieve sufficient dosing precision when dosing minute volume quantities, such as, for example, 1 nl (nanoliter) to 100 μl (microliters). In micromembrane pumps, the dosing precision is, for example, dependent on gas bubbles in the pump chamber, particles in the fluid, back pressure variations within the fluid channel, temperature variation and other influences.

Apart from the insufficient dosing precision of micromembrane pumps available at present, there are no systems, which may be implemented in an uncomplicated and thus cheap manner, to allow dosing and monitoring dosing of minute fluid quantities or fluid volumes in the nanoliter to microliter range. In addition, flow sensors, easy to implement, for the smallest volume packages in the nanoliter range have not been available up to now, or they do not have the accuracy needed for many applications, or are too expensive to integrate into the microdosing system. Apart from drug dosing mentioned above in medical technology, in many other fields of application, too, reliable and precise dosing and/or monitoring dosing of minute volume quantities are necessitated. Using liquid direct displacement devices in laboratory technology, charging the liquid fuel (such as, for example, methanol in DMFC=Direct Methanol Fuel Cell) in fuel cells or lubricant dosing in the form of lubricating bearings using oil are to be mentioned exemplarily in this regard.

In this context, reference is, for example, made to a liquid reservoir with level measurement and dosing system, withdrawal system and combined dosing/withdrawal system in the International publication WO01/84091 A1 and to the scientific publication "Dosierung and Messung kleiner Volumenströme als Voraussetzung für die Realisierung eines implantierbaren Mikroinfusionssystems" (Dosing and measuring small volumes streams as a requirement for realizing an implantable microinfusion system) by Bodo Nestler, et al., Zentrum für Biomedizintechnik der F H Lübeck in Impulse (10), 2005: ISSN 1618-5528, pages 65-73.

SUMMARY

According to an embodiment, a microfluidic device for detecting a flow parameter may have: a channel configured within a base body, said channel comprising a first inlet for feeding a first fluid and a second inlet for feeding a second fluid so as to form a fluid stream having the first and second fluids within the channel, and further comprising an output for providing the fluid stream on the output side, and said channel having a cross-sectional dimensioning for configuring within the channel, between a section of the channel that is filled with the first fluid and an adjacent section of the channel that is filled with the second fluid, a fluid interface between the first and second fluids that extends over the channel cross-section, a first feed means comprising a micropump associated with the first inlet for selectively feeding the first fluid to the channel, a second feed means associated with the second inlet for feeding the second fluid to the channel; and a detection means for detecting, on the basis of a different physical property of the first fluid and the second fluid within the channel, a measurement value (dependent on a current flow parameter of the first or second fluid; wherein the detection means is configured to capacitively detect a position of the fluid interface within the channel, and wherein two electrodes are arranged on the base body, said two electrodes being arranged opposite to each other with regard to the channel, so that an electric field that may be generated between the two electrodes exists both within that section of the channel that is filled with the first fluid and within that section of the channel that is filled with the second fluid, so that a change in the position of the fluid stream leads to a proportional change in capacitance between the two electrodes; or wherein the detection means is configured to resistively detect a position of the fluid interface within the channel, and wherein two electrodes are arranged on the base body, wherein a different electrical conductivity value exists within that section of the channel that is filled with the first fluid and within that section of the channel that is filled with the second fluid, so that a change in the position of the fluid stream leads to a proportional change in the electrical conductivity between the two electrodes.

According to another embodiment, a microfluidic dosing system for dosing minute quantities of a fluid may have: an inventive microfluidic device, a controller configured to selectively control the first feed means to feed in the first fluid or the second feed means to feed in the second fluid so as to obtain a predefined flow parameter of the first or second fluid within the channel, and a fluid separation means at the output of the channel for selectively separating the first fluid from the fluid stream provided at the output of the channel so as to obtain, downstream from the fluid separation means, an output-side fluid stream comprising the fluid.

According to another embodiment, a method of microfluidically dosing minute quantities of a fluid may have the steps of: selectively feeding a first fluid to a first inlet of a channel by means of micropump, and feeding a second fluid to a second inlet of the channel so as to form a fluid stream comprising the first and second fluids within the channel, and to further provide the fluid stream at an output of the channel, said channel having a cross-sectional dimensioning for configuring, between a section of the channel that is filled with the first fluid and an adjacent section of the channel that is filled with the second fluid, a fluid interface between the first and second fluids that extends over the entire channel cross-section, and detecting, on the basis of a different physical property of the first fluid and the second fluid within the channel, a measurement value dependent on a current flow parameter of the first or second fluid, controlling the first feed means to selectively feed the first fluid, and/or controlling the second feed means to selectively feed the second fluid so as to obtain a predefined flow parameter of the first and second fluids within the channel; separating the first fluid from the fluid stream provided at the output of the channel so as to obtain an output-side fluid stream comprising the second fluid, and controlling the first and/or second controller to stop feeding the second fluid to the channel on the input side when a fluid interface comprising a transition from the first fluid to the second fluid is detected at an intermediate position within the channel or at the channel output, so that a predefined quantity of the second fluid is present within the channel.

According to another embodiment, a microfluidic device for detecting a flow parameter may have: a channel configured within a base body, said channel comprising a first inlet for feeding a first fluid and a second inlet for feeding a second fluid so as to form a fluid stream having the first and second fluids within the channel, and further comprising an output for providing the fluid stream on the output side, and said channel having a cross-sectional dimensioning for configuring within the channel, between a section of the channel that is filled with the first fluid and an adjacent section of the channel that is filled with the second fluid, a fluid interface between the first and second fluids that extends over the channel cross-section, a first feed means comprising a micropump associated with the first inlet for selectively feeding the first fluid to the channel, a second feed means associated with the second inlet for feeding the second fluid to the channel; and a detection means for detecting, on the basis of a different physical property of the first fluid and the second fluid within the channel, a measurement value dependent on a current flow parameter of the first or second fluid; wherein the detection means comprises a plurality of individual sensor elements along the fluid channel that are configured to detect the different physical property of the first and second fluids in a spatially resolved manner at a plurality of positions along the channel that are associated with the individual sensor elements.

According to another embodiment, a microfluidic device for detecting a flow parameter may have: a channel configured within a base body, said channel comprising a first inlet for feeding a first fluid and a second inlet for feeding a second fluid so as to form a fluid stream having the first and second fluids within the channel, and further comprising an output for providing the fluid stream on the output side, and said channel having a cross-sectional dimensioning for configuring within the channel, between a section of the channel that is filled with the first fluid and an adjacent section of the channel that is filled with the second fluid, a fluid interface between the first and second fluids that extends over the channel cross-section, a first feed means comprising a micropump associated with the first inlet for selectively feeding the first fluid to the channel, a second feed means associated with the second inlet for feeding the second fluid to the channel; and a detection means for detecting, on the basis of a different physical property of the first fluid and the second fluid within the channel, a measurement value dependent on a current flow parameter of the first or second fluid; wherein at least one of the first and second inlets each have a disturbance detection means arranged thereat so as to detect accidental intrusion of the first fluid into the second inlet against the flow direction of the second fluid or accidental intrusion of the second fluid into the first inlet against the flow direction of the first fluid.

The present invention is based on the finding that a precise microfluidic detection of a flow parameter for precisely dosing a fluid, exemplarily in the range of nanoliters, and also corresponding dosing monitoring can be implemented and realized in a relatively uncomplicated manner by adding a first fluid (first flow medium) specifically to a second fluid (second flow medium) in a flow path (channel). Both fluids have the property that they do not mix, react or dissolve with each other immediately. Examples for these couples of fluids are e.g. air with water or oil with water. Since the cross-section dimensioning of the channel is selected such that a fluid interface between the first and second fluids within the channel forms between a section of the channel filled with the first fluid and an adjacent section of the channel filled with the second fluid, the fluid interface extending over the entire channel cross-section, the fluid stream within the fluid channel may then be monitored in a relatively uncomplicated manner by many different detection methods.

According to the invention, a different electrical conductivity, different dielectric conductivity (permittivity), different magnetic conductivity (magnetic permeability), different optical transparency or different optical reflectivity of the first and second fluids with regard to each other can be detected by means of a detection means in order to determine there from the necessitated flow parameter for monitoring dosing and controlling dosing, in the form of flow velocity, flow volume, flow direction, fluid propagation or transit time and/or filling quantity of the first or second fluid within the channel.

The detection means in the form of an array of sensors may exemplarily comprise a plurality of individual sensor elements along the fluid channel to detect the different physical properties of the first and second fluids in a spatially resolved manner at a plurality of positions along the channel associated to the individual sensor elements. In addition, a control means by means of which first and/or second feed means may be controlled may be provided so as to selectively feed the first or second fluid into the fluid channel.

A fluid channel or a sub-section thereof can preset an effective dosing volume for receiving a fluid. The fluid channel may then be filled with the second fluid specifically up to the preset dosing volume, whereupon the first fluid is fed to the fluid channel on the input side to provide the dosing quantity of the second fluid, which is in the channel on the output side at the channel output or exit, in a precisely dosed manner. This process is a self-adjusting dosing process in which the respective dosing volume is defined by the geometrical volume of the completely or partly filled channel and which may be repeated with high dosing precision as desired. In particular, it is pointed out that excess first fluid which is added to the second fluid in the channel for dosing and monitoring dosing can be removed from the fluid stream to be provided on the output side at a fluid separation means so that only the second fluid in a precisely dosed quantity is present at the channel output.

An alternative inventive procedure for exactly dosing a fluid is by generating a fluid stream (including the first and second fluids), which can be monitored with regard to the flow parameter, in the fluid channel by specifically feeding the first fluid into a continuous flow of a second fluid in the fluid channel, exemplarily in predetermined intervals and in a predetermined quantity, by means of a micropump and/or micromembrane pump. This allows determining the propagation time of the first and second fluids within the channel by means of the detection means.

In particular, a predetermined ratio between the first and second fluids, exemplarily also at a predetermined flow velocity, can also be fed into the fluid channel and be detected precisely in terms of measuring technology, as far as the first and second fluids in the fluid stream exhibit mutually different physical properties which can be detected in terms of measuring technology and the fluid interface(s) form/s in the fluid channel.

Furthermore, the inventive concept allows feeding a predefined quantity of the first fluid in a (exemplarily continuous) stream of the second fluid into the channel on the input side, wherein the ratio between the first and second fluids in the fluid stream may be adjusted and/or controlled. This in turn allows realizing dosing of a predetermined dosing quantity of the second fluid per unit of time and monitoring same relatively easy in accordance with the invention. In particular, the fluid separation means may be employed for separating the first fluid from the fluid stream again.

The control means for the first and/or second feed means may additionally be configured to evaluate a measurement value detected by the detection means with regard to the current flow parameter (actual value), whereupon the first and/or second feed means can be controlled based on a deviation of the current flow parameter (actual value) from the predetermined flow parameter (set value) to set the predefined flow parameter and thus precise dosing of the first and/or second fluids in the channel.

In accordance with the invention, a dosing system for dosing minute volume quantities and for monitoring dosing these minute dosing quantities (fluid quantities), such as, for example, for being used in medical technology for drug dosing, in laboratory technology, in fuel cells or in lubricant dosing can be realized in an extremely uncomplicated and reliable manner using the control means which may be coupled to the microfluidic device for detecting a flow parameter.

Another advantage of the invention is the fact that by reducing the channel dimensions (cross section, especially channel height) the measurement resolution can be increased significantly. E.g., if the height h of the measurement channel is reduced, the measurement signal per length of a capacitive measurement method will be increased (capacitance C~1/h), and the volume/length form factor of the channel will be decreased. For this two reasons, the flow measure accuracy is increasing at low flow rates.

BRIEF DESCRIPTION OF THE DRAWINGS

Embodiments of the present invention will be detailed subsequently referring to the appended drawings, in which:

FIGS. 7a-c show a schematic illustration of an exemplary implementation of a first and second fluid feed means for the microfluidic dosing system in accordance with another embodiment of the present invention;

DETAILED DESCRIPTION OF THE INVENTION

Figure 1A:
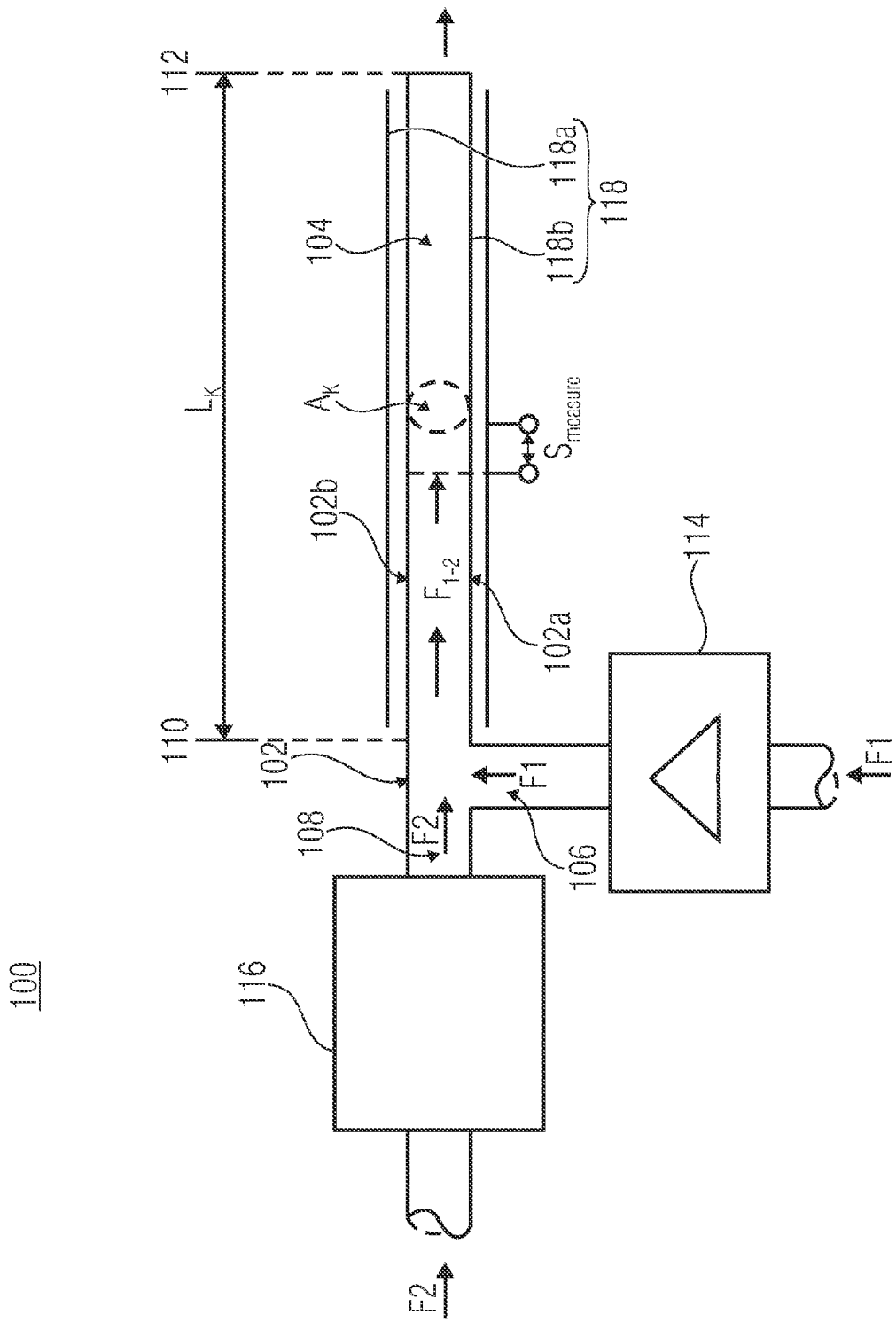
FIGS. 1a-b show schematic fundamental illustrations of a microfluidic device for determining a flow parameter in accordance with an embodiment of the present invention.

Before discussing the present invention in further detail using the drawings, it is pointed out that in the figures identical elements, elements having the same function or the same effect are provided with same reference numerals so that the description of these elements and the functionality thereof illustrated in the different embodiments is mutually exchangeable or may be applied to one another in the different embodiments.

Subsequently, a first general embodiment of an inventive microfluidic device 100 for detecting a flow or stream parameter or dosing parameter will be described using FIG. 1a for a general discussion of the functional context.

As is depicted in FIG. 1a, the microfluidic device includes a channel 104 formed in a base body 102. On the input side, the channel 104 comprises a first inlet 106 for feeding a first fluid F1 and a second inlet 108 for feeding a second fluid F2 into a fluid input 112 so as to form a fluid stream $F_{1-2}$ comprising the first and second fluids F1, F2 within the fluid channel 104. The fluid stream $F_{1-2}$ is provided on the output side to an output or exit 112 of the channel 104. In accordance with the present invention, that respective regions where the first and second fluids F1, F2 are fed into the channel 104 are considered as first and second channel inlets 106, 108.

The channel 104 comprises a cross-sectional area $A_K$ and a cross-sectional dimensioning to form, between a section of the channel 104 filled with the first fluid F1 and an adjacent section of the channel 104 filled with the second fluid F2, a fluid interface between the first and second fluids F1, F2 in the channel which extends over the entire channel cross-section.

As is exemplarily depicted in FIG. 1a, the channel exhibits a channel length $L_K$ between the channel input 112 and the channel output 110. In addition, the channel 104 exemplarily comprises, as is depicted in FIG. 1a, a round channel cross-section $A_K$, wherein, as the following expositions will show, however, basically any cross-sectional shapes of the channel 104 may be selected as long as the fluid interface mentioned before forms between the first and second fluids F1, F2.

Additionally, it has to be kept in mind that, with regard to FIG. 1a, that region of the channel 104 where, downstream of the first and second inlets 106, 108, the first and second fluids F1, F2 are contained together in the fluid channel 104 is referred to as channel input 110.

As is additionally depicted in FIG. 1a, the microfluidic device 100 includes a first feed means 114 comprising a micropump associated to the first inlet 106 to selectively feed the first fluid F1 into the channel 104. Additionally, the microfluidic device 100 comprises a second feed means 116 associated to the second inlet 108 to feed the second fluid F2 into the channel 104. The second feed means 116, too, may comprise a second micropump for selectively feeding the second fluid F2 into the channel 104.

Micromembrane, or microdiaphragm, pumps the membranes, or diaphragms, (micromembranes or microdiaphragms) of which for transporting the fluid in a predetermined direction are driven by a predetermined or adjustable pump stroke or diaphragm excursion, exemplarily by means of a piezoelectric element which may be enabled electrically, are exemplarily used as micropumps or micromembrane pumps for the first and second feed means 114, 116. Depending on the electrical excitation, the stroke volumes of micromembrane, or microdiaphragm, pumps may exemplarily be generated in a range from 10 nanoliters to 100 mlcroliters per pump process.

When the first feed means 114 is configured to feed the first fluid, such as, for example, a gas or air, from an environment or ambient atmosphere to the first inlet 106 of the fluid channel 104, a filter element may be provided upstream of the feed means 114 in the flow direction of the first fluid F1 to filter out potential contaminations or other undesired substances from the fluid F1 to be fed before feeding same to the fluid channel 106.

The microfluidic device 100 additionally includes detection means 118 which is exemplarily formed by first and second measuring electrodes 118a, 118b in order to detect a measurement value $S_{MEASURE}$ dependent on a current flow parameter of the first or second fluid F1, F2, based on a different physical property of the first fluid F1 and the second fluid F2 in the channel 104. The detection means 118 may be configured to detect a position or change in the position of the fluid interface in the channel 104 on the basis of the different physical properties of the first and second fluids F1, F2, wherein the current flow parameter of the first or second fluid F1, F2 may be determined from the position or change in the position of the fluid interface within the channel 104.

In the present invention, a fluid means a gas (a compressible fluid) or a liquid (an incompressible fluid). The general term "fluid" is used since most physical laws apply equally for gases and liquids. In the present invention, both a gas or a liquid may generally be used for both the first fluid and for the second fluid, as long as the boundary conditions, to be discussed below, with regard to the necessitated formation of a fluid interface between the first and second fluids are fulfilled.

Generally, the position and shape of the fluid interface depend on gravity on the one hand and interfacial tensions between the first and second fluids F1, F2 and between the fluids and the material of the base body 102 in which the fluid channel 104 is formed, on the other hand. In accordance with the present invention, the cross-section dimensioning of the channel 104 is selected such that the shape and configuration of the fluid interface are determined, above all, by the interfacial tensions and no longer by gravity and other acting forces, such as, for example, rotational forces, vibrational forces, magnetic forces etc. Depending on the fluid characteristics and the channel material the interfacial tension will exemplarily, with channels 104 with a circular cross-section of diameters of smaller than 0.01 mm up to 3 mm, predominate relative to gravity. Neither does gravity play an important role in any other position or orientation of the fluid channel 104 so that the fluid interface will not change its position significantly due to external ambient influences and force effects. As is depicted in FIG. 1a, the channel 104 may exemplarily be configured to be circular or also rectangular with a rectilinear orientation between the input 110 and the output 112.

However, it is pointed out that the cross-section dimensioning of the channel 104 need not necessarily be constant over the length $L_K$ of the channel 104. Potential changes in the cross-section (expansions or contractions) may easily be accommodated when determining a measurement value and be taken into consideration when determining the flow parameter using determining a position or when determining a change in the position of the interface in the channel 104.

Additionally, the channel 104 may also be configured to be of a meander shape or a helix shape so as to correspondingly adjust a predetermined filling quantity or a predetermined filling volume of the effective channel region as a product of the channel length $L_K$ and the (average) channel cross-sectional area $A_K$.

Thus, depending on the case of application, a fluid channel of a predetermined maximum filling volume (volume between channel input and output) may be used since a fluid interface forming, the position of which in the channel shape is basically independent of gravity, does not depend on the cross-sectional area of the channel but the shape of the channel cross-section, more precisely the smallest dimension of the channel cross-section.

When, for example, the channel is of an elliptical or circular cross-sectional dimensioning, the small axis of the elliptical cross-section or the diameter of the circular cross-section may be selected such that the position of the fluid interface is basically determined by the interfacial tension of the second fluid which has a higher viscosity than the first fluid, and by the interfacial tension between the second fluid and the material of the channel wall.

When, however, the channel 104 is of a rectangular cross-sectional dimensioning, the smaller side of the rectangular cross-sectional dimensioning or a side of a squared cross-sectional dimensioning may be selected such that the position of the fluid interface is basically determined by the interfacial tension of the second fluid (of the, compared to the first fluid, higher viscosity), and by the interfacial tension between the second fluid and the material of the channel wall.

It is to be kept in mind in this context that the channel and, optionally, the feeds may be formed as simple tube elements, glass capillaries or even as high-precision patterns in a semiconductor substrate, such as, for example, a silicon substrate, comprising the respective integrated detection, evaluation and/or control electronics.

Glass capillaries provide a good trade off between the requirement of providing a highly precise dosing volume and causing reduced costs due to a relatively inexpensive (but very precisely performable) fabrication process. Thus, a fluid channel 104 in form of a glass capillary can be advantageously used as a disposable ("one-way") mass article for precisely dosing minute quantities of drugs, especially for a medical treatment of patients with insulin.

With regard to the fluidic properties of the fluids F1, F2 used, it should be kept in mind that at least during the duration or period when they are located in the channel 104 for dosing, there is basically no or only limited mixing of these fluids, i.e. the fluids are to be non-miscible. For the exemplary case in which one of the fluids is a gas and the other fluid is a liquid, it has to be kept in mind that one potential disturbing quantity when detecting the flow and/or dosing parameter is evaporation of the liquid and absorption in the gas until the gas used is, for example, saturated. Evaporation occurs, above all, at the fluid interface between the two media, wherein in a liquid-gas interface, this is also referred to as a "meniscus".

The evaporation rate (or the inverse effect, the condensation) has the effect of a small undesired movement of the fluid interface, even though neither the first nor the second fluid F1, F2 is fed. The evaporation rate, i.e. the quantity of liquid transitioning to the gaseous phase per unit of time, depends, apart from the saturation of the gas with liquid molecules (humidity in the case of water and air for the fluids F2 and F1), above all, on the size of the free surface between the liquid and the gas. Thus, the smaller the diameter or cross-sectional area of the channel 104, the smaller is the disturbing evaporation.

In order to be able to achieve the most reliable and exact detection precision possible of the flow parameter of the first or second fluid F1, F2 in the microfluidic channel, in accordance with the invention, fluids, i.e. gases or liquids, are used for the first and second fluids F1, F2 in which there is no, or only tolerable, mixing, chemical reacting or evaporation/condensation between the two fluids during the duration of their presence in the channel 104, for example during dosing and respective measuring. This can be achieved by minimizing the free surface and by minimizing the measurement time.

One advantage of re-guiding the first fluid F1 in a closed loop channel 122 to the inlet 110 would be the first fluid F1 will be nearly saturated by molecules of the second F2. In the case of air as the first fluid F1 and a liquid as the second fluid F2, after a defined time period the no further evaporation occurs.

Especially for implantable drug delivery systems this would be important. In that case, also the drug as the second fluid F2 within a drug reservoir 126, should be supplied in a manner that it is nearly saturated with the gas as the first fluid F1, with that an evaporation of the drug F2 into the gas F1 or an dissolving of the gas F1 into the drug F2 will be minimized. Together with a defined body temperature and small exchange area (meniscus, cross section) the exchange between the gas F1 and the drug F2 will be reduced to a minimum value and the implanted system can work for a long time.

In addition, the first and second fluids are to be selected such that they comprise different physical properties which may be determined by means of the detection means so that a position or change in the position of the fluid interface in the channel is detectable based on the different physical properties of the first fluid and the second fluid. The current flow parameter of the first or second fluid F1, F2 may then be determined from the position or the change in the position of the fluid interface. Thus, the different physical properties may be a different electrical conductivity, a different dielectric conductivity (permittivity), a different magnetic conductivity (permeability), a different optical transparency or a different optical reflectivity of the first fluid F1 and the second fluid F2 to each other. However, any different physical properties of the first and second fluids which may be detected in the fluid channel in a spatially resolved manner, may be used for dosing control and monitoring.

The current flow parameter detected in the channel 104 may exemplarily indicate flow velocity, flow volume, flow direction, fluid propagation or transit time and/or a filling level of the first or second fluid F1, F2 in the channel 104.

The detection means 118 may exemplarily comprise a plurality of individual sensor elements which are arranged along the fluid channel 104 at a predetermined number, size and distribution per length section. The individual sensor elements are thus configured to detect the different physical properties of the first and second fluids F1, F2 at a plurality of position associated to the individual sensor elements along the channel 104 in a spatially resolved manner.

When, exemplarily, the first and second fluids F1, F2 comprise different dielectric conductivities $\in_{R1}$, $\in_{R2}$, exemplarily, the detection means 118 may be configured to capacitively detect the measurement value relative to the current flow parameter of the first or second fluid F1, F2. Two electrodes 118a, 118b electrically insulated from each other and from the fluid stream $F_{1-2}$ are exemplarily arranged at the base body 102, wherein the two electrodes 118a, 118b are arranged so as to be opposite each other relative to the channel 104. This allows achieving an electrical field which may be generated between the two electrodes 118a, 118b to be present in both the section of the channel 104 filled with the first fluid F1 and in the section of the channel 104 filled with the second fluid F2, wherein a change in position in the fluid stream results in a proportional change in capacitance between the two electrodes 118a, 118b.

It is to be pointed out in this context that in the inventive concept, detecting a position or change in the position of a fluid interface, due to the relatively small channel dimensions, can be supplemented in a nearly optimum way with a capacitive measuring principle, since a capacity measured is the greater, the smaller the distance between the capacity electrodes. In addition, the fluid interface is the more stable, the smaller the dimensions of the channel 104. However, for the capacitive measuring principle, it has to be kept in mind that, depending on the geometry, the dielectric parameters $\in_{R1}$, $\in_{R2}$ of the first and second fluids F1, F2 are to be sufficiently different in order to achieve the greatest possible sensitivity in the form of a sufficiently great change in capacitance when moving the interface in the channel. In case of air the dielectric parameters is $\in_{air}=1.00058$, in case of water the dielectric parameters $\in_{water}=81$, and oil is around $\in_{oil}=2\ldots 2.5$.

Typically, the cover and electrical isolation between the fluids and the electrodes is made from plastics, here the $\in_{plastics}=1.5\ldots 3$, depending on the type of plastics. To maximize the capacitance, the thickness of the cannel cover should be chosen as thin as possible, e.g. between 20 µm to 200 µm.

In addition, the first and second electrodes 118a, 118b may each consist of a plurality of individual electrodes (not shown in FIG. 1) such that a plurality of individual capacitances is formed between the first and second electrodes 118a, 118b, wherein these individual capacitances may be read out and detected independently of one another, and additionally a respective predetermined position in the channel 104 may be associated to a single capacitance value determined.

As the above expositions are to clarify, a linear connection between the filling ratio of the channel 104 comprising the first and second fluids F1, F2 may exemplarily be obtained, wherein the detected capacitance value changes linearly with the filling quantity of the first or second fluid F1, F2 in the channel. Equally, it is possible, when using a plurality of individual electrodes for the first and second electrodes 118a, 118b, to specifically determine and/or associate to the capacitance determines the presence of the first or second fluid F1, F2 or an interface between same at a position associated by a single capacitance.

When the channel is, for example, configured to be rectangular, the first and second electrodes 118a, 118b may be arranged horizontally relative to first and second main surfaces 102a, 102b of the base body 102 and may at least partly cover the channel 104. Alternatively, the first and second electrodes 118a, 118b may be arranged vertically relative to the first and second main surfaces 102a, 102b of the base body 102 and extend along the channel. The latter design is exemplarily shown in FIG. 1a.

When the channel 104 is, for example, configured to be circular or elliptical in the base body 102, the first and second electrodes 118a, 118b may each extend, at least for a section, along a curved external surface of the channel 104. When, for example, the channel is configured to be a pipe or tube of a circular cross-section, the first and second electrodes 118a, 118b may exemplarily be arranged around the base body 102 of the channel 104 in a basically semi-cylindrical form, which is how the electrical field strength caused in the channel 104 for measuring and, thus, the measuring precision may be increased considerably since at least a great part of the electrical field lines penetrate the channel 104.

As has been mentioned before, apart from a different dielectric conductivity of the first and second fluids F1, F2, a different electrical conductivity of the first and second fluids relative to each other may also be used. In this case (not shown in FIG. 1a), two electrodes which relative to the channel 104 are opposite each other are exemplarily arranged on the body for measuring the conductivity of the fluid stream comprising the first and second fluids F1, F2 in the channel 104, the electrodes being in electrical contact with the fluid stream $F_{1-2}$ so that an electrical conductivity value and/or resistance value may be detected between the two electrodes. The respective position of one or several fluid interfaces or even the presence of the first or second fluid in the channel and/or in a section of the channel may be determined in this way. Such electrodes provided for measuring the electrical conductivity and/or resistance may again each include a plurality of individual electrodes so that a conductivity value and/or resistance value may be detected between the respective associated individual electrodes of the first and second electrodes in a position-dependent manner.

The measuring principles mentioned above may equally be applied to detecting different magnetic conductivities of the first and second fluids F1, F2 to detect the current flow parameter in the channel 104 in an, advantageously, position-dependent manner, as long as the measuring quantity, i.e. the magnetic conductivity of the first and second fluids F1, F2, is influenced by the channel section filled with the first fluid F1 in a manner different from that in the channel section filled with the second fluid F2.

When, exemplarily, the base body 102 is configured to be translucent (or transparent for other electromagnetic radiation) in the region of the length $L_K$ of the channel 104, different optical properties of the first and second fluids F1, F2, such as, for example, a different optical transparency or optical reflectivity, may be made use of to detect a position or change in the position of one or several fluid interfaces in the channel, wherein the current flow parameter of the first or second fluid F1, F2 may be determined from the position or change in the position of the fluid interface(s). When, exemplarily, a transparency measurement is performed, respective radiation-emitting elements (such as, for example, LEDs, OLEDs etc.) and corresponding radiation-detecting elements (both not shown in FIG. 1a) are to be arranged at opposite sides of the base body 102 to detect different optical transparency values along the channel length $L_K$ in a spatially resolved manner. When, exemplarily, an optical reflectivity of the first and second fluid F1, F2 is detected along the channel length $L_K$ of the channel 104, the base body 102 is to be configured to be transparent, at least on one side, for the corresponding electromagnetic radiation (such as, for example, light of a predetermined wavelength) to the fluid stream $F_{1-2}$ in the channel 104.

Further designs and additional functional elements which may optionally be added to the microfluidic device illustrated in FIG. 1a and the functionality thereof in cooperation with the functional elements described before will be described subsequently referring to FIG. 1b.

Figure 1B:
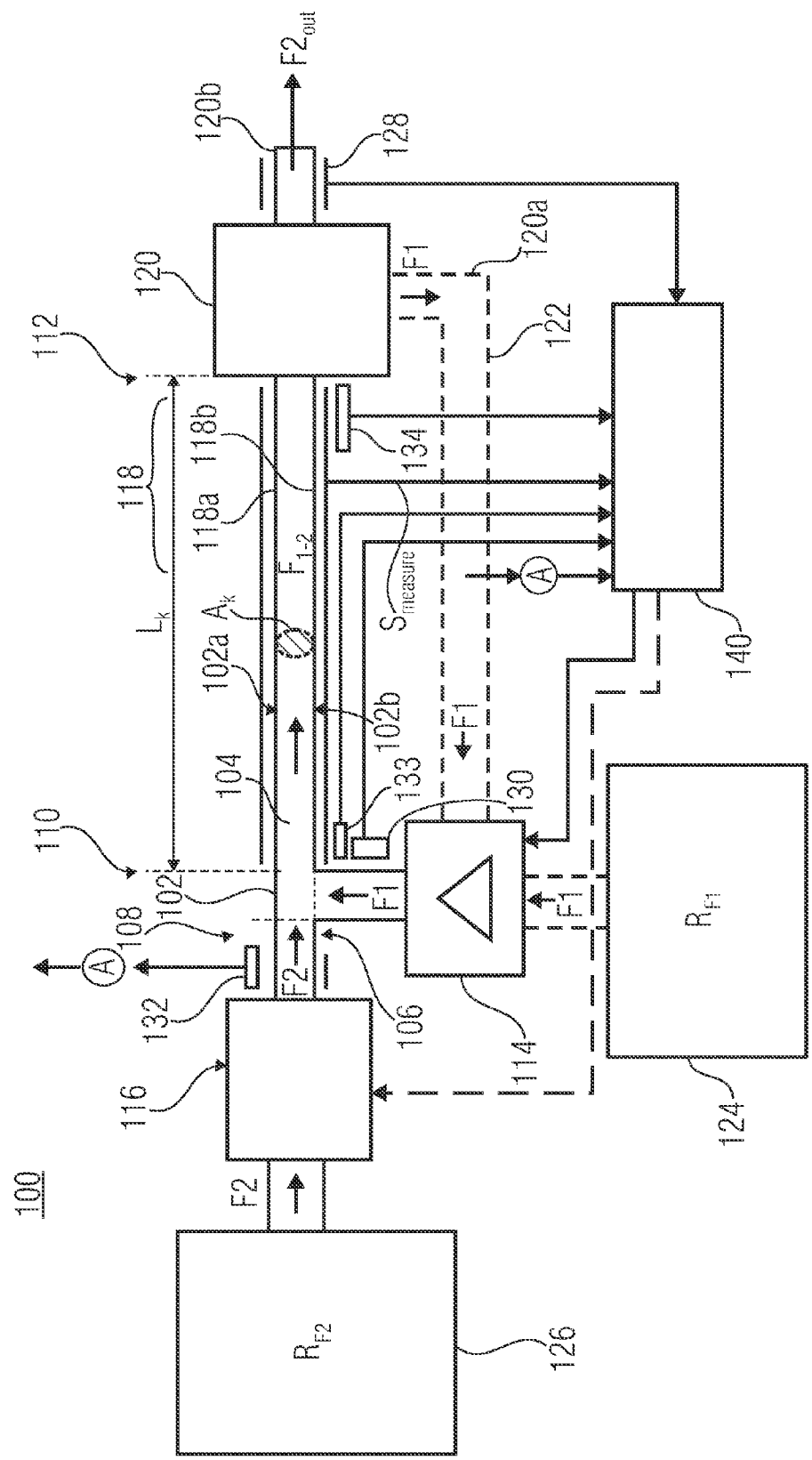

As is depicted in FIG. 1b, the inventive microfluidic device exemplarily comprises, at the output 112 of the channel 104 fluid separation means 120 for selectively separating the first fluid F1 from the fluid stream $F_{1-2}$ provided at the output 112 of the channel 104. As is depicted in FIG. 1b, the fluid separation means 120 is arranged to be directly adjacent to the output 112 of the channel 104. By arranging the fluid separation means 120 directly adjacent to the channel output 112, a so-called dead volume, i.e. a volume which is not included in the volume measurement, between the channel output and the fluid separation means may be minimized or eliminated. However, it is of course also feasible to arrange the fluid separation means 120 in a manner spaced apart from the channel output 112 when the dead volume resulting by this has a negligible influence on the measuring result $S_{MEASURE}$ detected by the detection means 118.

As is depicted in FIG. 1b, the fluid separation means 120 may exemplarily be coupled to the first inlet 106 or the first feed means 114 associated to the first inlet 106 via a fluid path 122 to form a closed cycle for the first fluid F1 from the fluid separation means 120 to the first inlet 106 of the channel 104. This is advantageous e.g. if the microdosing system has to be be separated from ambient surrounding, e.g. in implantable drug delivery systems. When, exemplarily, the first fluid F1 is configured to be a gas, such as, for example, an ambient gas or air, the fluid separation means 120 may also be configured to output the first fluid F1 to the ambient atmosphere whereas the first feed means 114 may be configured to withdraw the first fluid F1 from an ambient atmosphere, such as, for example, air and to feed same selectively to the first inlet 106 or channel input 110. Of course, the first fluid F1 may also be withdrawn from an optional reservoir 124 for the first fluid F1. Equally, a reservoir 126 for the second fluid F2 may be provided at the second feed means 116 associated to the second channel input 108 to feed the second fluid F2 via the second feed means 116 to the second channel input 108.

The fluid separation means 120 may exemplarily be realized by providing a fluid separation chamber (for separating the first fluid F1) of a chamber height which exemplarily is equal or larger than the diameter of the channel 104 and exemplarily corresponds to 1.0 to 2 times the diameter of the channel 104, wherein the chamber (not shown in FIG. 1b) is bordered by a hydrophobic (liquid-repelling) filter diaphragm of small pore diameter.

For medical applications, it is advantageous to use a pore size of about 0.2 µm, i.e. about 0.1 to 0.3 µm (considering the "Bubble-point" method). Such a pore size prevents bacteria or virus entering the fluid path via the hydrophobic filter diaphragm. The bubble point method is used for pore size determination. It is based on the fact that, for a given fluid and pore size with a constant wetting, the pressure necessitated to force an air bubble through the pore is inverse proportion to the size of the hole.

A second advantage of this small pore size of the hydrophobic gas separation filter, which is advantageous both for medical applications and lubrication dosing, is that there is a bubble point of several hundred kPa, which is greater than the highest overpressure occurring at the gas separator. For example, within a drug delivery system, a typical stall pressure to be generated by the drive needed to flush a blocked catheter is about 100 kPa. Typical over pressure needed to dose oil or lubricants to machine spindles or bearings are 50 kPa.

From two reasons, it is advantageous to minimize the area of the hydrophobic filter diaphragm: first, a small diaphragm is more stable against overpressure, and second the contact area between F1 and F2 is minimized to minimize evaporation and/or condensation between the fluids, e.g. if the microdosing system is out of operation.

This filter diaphragm is impermeable to the second fluid F2 (for example a liquid), i.e. comprises a so-called great bubble point, so that the pores of the filter diaphragm do not wet with the second fluid F2 (e.g. comprising a higher viscosity than the first fluid F1). Due to the fact that the meniscus usually extends over the entire channel cross-section, the first fluid F1 will in all cases contact the filter diaphragm repelling the second fluid F2. The overpressure (generated by the feed means 114 or 116) acting in the separation chamber, exemplarily by the first and/or second feed means 114, 116, in connection with the suction negative pressure of the separation chamber by the first feed means 114 (of the first fluid F1) results in a reliable separation of the first fluid F1, exemplarily bubble separation if the first fluid F1 is gaseous, from the fluid stream $F_{1-2}$. The separation chamber may have drop-shaped or curved inner dimensions.

Since a contraction relative to the fluid channel 104, such as, for example, a capillary contraction, is present in the fluid separation means 120 anyway, a preloaded film, such as, for example, a silicon film, which only yields at a defined overpressure relative to the fluid stream $F2_{OUT}$ provided on the output side and releases the output-side fluid flow, may be employed at this bottleneck in the fluid separation means 120 or, for example, on the output side at the fluid separation means 120. A so-called free flow protection may thus be exemplarily integrated in the fluid separation means 120.

The fluid separation means 120 comprises a first output 120a for providing the first fluid F1 separated from the fluid stream $F_{1-2}$ and another output 120b for providing the output-side fluid stream in the form of the second fluid $F2_{OUT}$ on the output side. In order to detect whether at least residual quantities of the first fluid F1 are still, in an undesired way, present in the output-side fluid stream $F2_{OUT}$, further detection means 128 may be provided at the second output 120b of the fluid separation means 120 to detect whether a quantity of the first fluid F1, after flowing through the fluid separation means 120, is still present in the output-side fluid stream $F2_{OUT}$. Additionally, the further detection means 128 may be configured to quantitatively detect the quantity of the first fluid F1 present in the output-side fluid stream $F2_{OUT}$. Thus, the second output 120b (or the following channel) and the further detection means 128 may be configured in correspondence with the detection means 128 and the fluid channel 104 described before.

The inventive microfluidic device 100 illustrated in FIG. 1b may additionally comprise a first disturbance detection means 130 on the input side, i.e. at the first inlet 106, and a second disturbance detection means 132 at the second inlet 108. The first and second disturbance detection means 130, 132 are each configured to detect accidental intrusion of the first fluid F1 into the second inlet 108 against the flow direction of the second fluid F2 and/or accidental intrusion of the second fluid F2 into the first inlet 106 against the flow direction of the first fluid F1. With regard to the functionality of the first and second disturbance detection means 130, 132, they may again be configured in analogy to the detection means 118, wherein a disturbing or accidental intrusion of the first or second fluid into the respective opposite fluid inlet may be detected using the different physical properties of the first and second fluids in the form of a different electrical conductivity, permittivity, permeability, transparency or reflectivity of the first and second fluids.

Optionally, a hydrophobic (liquid- or water-repellent) filter diaphragm having a small pore diameter is arranged as a protection means in the first inlet 106 for feeding the first fluid F1 to the channel inlet 110. The filter diaphragm is permeable for the first fluid F1 (e.g. in the form of a gas) and is impermeable for the second fluid F2 (e.g. in the form of a liquid). The pores inside the hydrophilic filter membrane are not wetted, as there is only gas inside the pores. Thus, it is ensured that the second fluid F2 can not enter the first inlet 106 of the first fluid F1. In this case, the first disturbance detection means 130 at the first inlet 106 may be omitted.

As has already been discussed before with regard to the detection means 118, same may be provided to detect the presence or passing of a fluid interface at a predetermined pair of individual electrodes of the first and second electrodes 118a, 118b. The detection means 118 may particularly also be used to detect the presence or passing of the fluid boundary at a predetermined intermediate position in the fluid channel 104 or even at the channel output 112. Optionally, further detection means 133, 134 may be provided at the channel inlet 110 and/or the channel output 112 of the channel 104 to fulfill this functionality of detecting the presence or passing of the fluid boundary at the channel inlet 110 and/or the channel output 112. The further detection means 133, 134 may thus again make use of the different physical properties of the first and second fluids F1, F2 (corresponding to the functionality of the detection means 118).

The inventive microfluidic device 112 for detecting a flow or dosing parameter may additionally comprise a controller 140 or be coupled thereto. The controller 140 is configured to control, or regulate, the first feed means 116 and, in particular, the micropump or micromembrane pump used here to feed the first fluid F1 selectively to the channel 104 via the first inlet 106. When the second feed means 116 itself is equipped with the second micropump (not shown in FIG. 1b), the controller 140 may additionally be configured to control the second feed means selectively for feeding the second fluid F2 to selectively feed the second fluid F2 to the channel input 110. Thus, the controller 140 may be configured to obtain the fluid stream $F_{1-2}$ of the first and second fluids F1, F2 in the channel 104 at a predefined flow parameter (set value). The control means 114 may additionally be configured to evaluate the measurement value $S_{MEASURE}$ detected by the detection means 118 and to determine the current flow parameter (actual value), and to additionally control the first and/or second feed means 114, 116 based on an determined deviation of the determined current flow parameter from the predetermined flow parameter so as to obtain the predefined flow parameter of the first and/or second fluid F1, F2 in the channel 104.

Furthermore, the controller 140 may be configured to accept and evaluate the measuring signals provided by the further detection means and/or disturbance detection means 128, 130, 132, 133 and 134, to selectively and specifically control the first and/or second feed means 114, 116. It should be kept in mind in this context that processing means (not shown in FIG. 1) may be associated to the controller 140 internally or externally to perform the processing and evaluating processes or steps necessitated.

In particular, the controller 140 may be employed to specifically control feeding of the first fluid F1 and the second fluid F2 into the fluid channel 104, wherein, using the fluid separation means 120, a highly precisely dosed discharge quantity of the second fluid F2 is provided as the output-side fluid stream $F2_{OUT}$. With regard to using the inventive microfluidic device 100 for detecting a flow or dosing parameter in a microfluidic dosing system, reference is made to the following expositions regarding FIGS. 3-5.

Subsequently, another alternative embodiment of a microfluidic device 200 for detecting a flow or dosing parameter in accordance with another embodiment will be discussed making reference to FIGS. 2a-b. With regard to the further description regarding FIGS. 2a-b, it is pointed out that elements of the microfluidic device 200 which are identical in their function, are of the same function or are of the same effect as those elements of the microfluidic device 100 illustrated in FIGS. 1a-b are still provided with the same reference numerals.

Figure 2A:
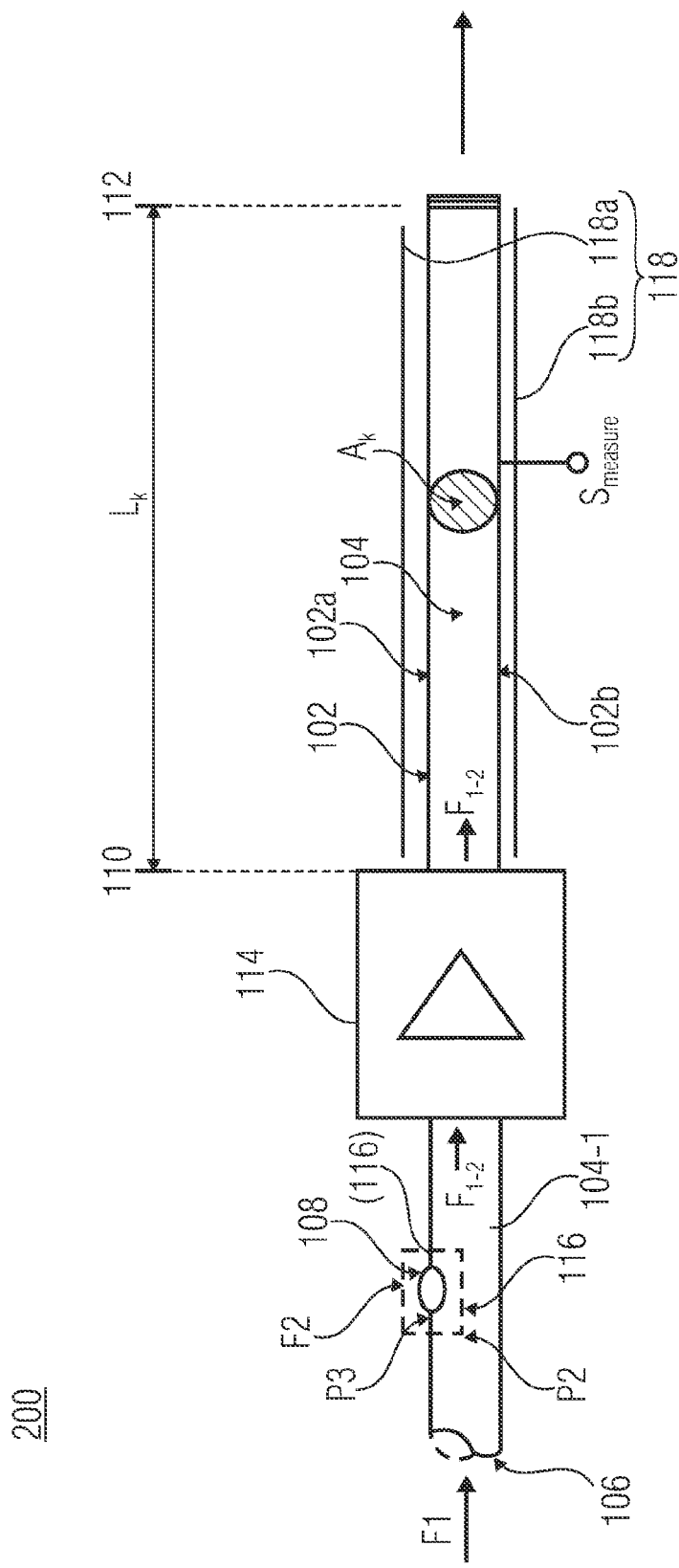
FIG. 2a-b show schematic fundamental illustrations of a microfluidic device for detecting a flow parameter in accordance with another embodiment of the present invention.

As is depicted in FIG. 2a, the microfluidic device 200 for detecting a flow parameter comprises a channel 104 formed in a base body 102. The base body exemplarily again comprises first and second main surfaces 102a, 102b. The channel 104 comprises a first inlet 106 for feeding a first fluid F1 and a second inlet 108 for feeding a fluid stream $F_{1-2}$ comprising the first and second fluids F1, F2 in the channel 104, and additionally an output 112 for providing the fluid stream $F_{1-2}$ on the output side. The channel 104 again comprises a cross-sectional dimensioning to form a fluid interface between the first and second fluids F1, F2 which extends over the entire channel cross-section, in the channel 104 between that section of the channel filled with the first fluid F1 and an adjacent section of the channel filled with the second fluid F2. The microfluidic device 200 additionally comprises first feed means 114 comprising a micropump, which is associated to the first inlet 106, for selectively feeding the first fluid F1 into the channel 104. Additionally, the microfluidic device 200 comprises second feed means 116, which is associated to the second inlet 108, for feeding the second fluid F2 into the channel. Additionally, detection means, exemplarily comprising first and second detection sections 118a, 118b, is provided for detecting a measurement value $S_{MEASURE}$ depending on a current flow parameter of the first and second fluids F1, F2 based on a different physical property of the first fluid F1 and the second Fluid F2 in the channel 104. The first feed means 114 and the second feed means 116 implemented to include an opening 108 are arranged on the input side at the channel 104. Thus, the second feed means 116 is, in the flow direction of the fluid stream $F_{1-2}$, arranged upstream of the first feed means 114. The second feed means 116 is arranged as an opening 108, in the channel section for feeding the second fluid F2 such that, with a (e.g. every) diaphragm excursion of the micropump of the first feed means 114, a quantity of the second fluid (together with the first fluid) is injected into the channel 104 at the inlet 110 so as to form the interface between the first fluid F1 and the second fluid F2. The ratio between the quantities of first and second fluid can be defined by the flow resistance and the geometry of the inlet 108.

Figure 2B:
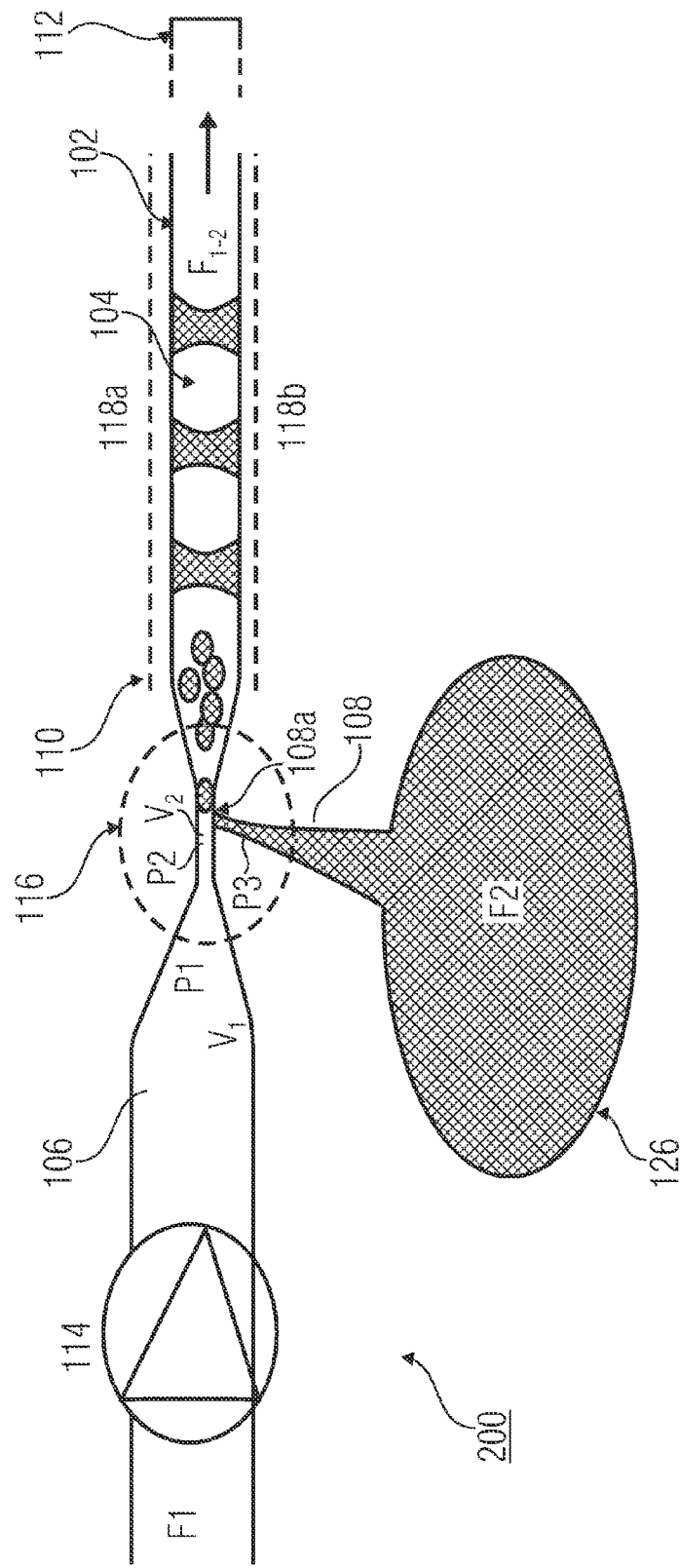

The alternative microfluidic device 200 for detecting a flow parameter, as is depicted using FIGS. 2a-b, allows omitting second feed means 116 in the form of another micropump, wherein the second feed means 116 implements a mixer structure which sucks in or injects the second fluid F2 into the first fluid F1 to be dosed. Thus, a small opening or a small hole may be formed in the base body 102 to the channel 104, exemplarily in the flow direction upstream of the first feed means 114 formed as a micropump, wherein the opening is configured to be of a size such that a small quantity (e.g. a droplet) of the second fluid F2 (such as, for example, a small gas bubble) is injected into the stream path with the suction strokes by the micropump of the first feed means, i.e. when there is a negative pressure in the suction line 104-1 (e.g. if the pressure value P2 of the first fluid F1 at the first inlet 106 falls below the pressure value P3 of the second fluid F2 at the second inlet 108). These small injected quantities of the second fluid F2, exemplarily in the form of gas bubbles, may then, as will the subsequent discussion show clearly, be used for measuring a flow parameter of the fluid stream $F_{1-2}$ within the channel 104. The opening 108 is either selected to be so small that the second fluid F2 cannot escape from it, or a valve element, such as, for example, in the form of a film over the opening, may be used.

As depicted in FIG. 2b, the microfluidic device 200 detecting a flow parameter comprises a channel 104 formed in a base body 102. The channel 104 comprises a first inlet 106 for feeding a first fluid F1, and a second inlet 108 for feeding a second fluid F2 into the inlet 110 of the channel 104, and additionally an output 112 for providing the fluid stream $F_{1-2}$ on the output side. The channel 104 again comprises a cross-sectional dimensioning to form a fluid interface between the first and second fluids F1, F2 which extends over the entire channel cross-section, in the channel 104 between that section of the channel filled with the first fluid F1 and an adjacent section of the channel filled with the second fluid F2.

The microfluidic device 200 additionally comprises the first feed means 114, for example in form of a micropump, which is associated to the first inlet 106, for selectively feeding the first fluid F1 into the channel inlet 110. Additionally, the microfluidic device 200 comprises a second feed means 116, which is associated to the second inlet 108, for feeding the second fluid F2 into the channel inlet 110. Additionally, the detection means 118, exemplarily comprising first and second detection elements (or an array of detection elements) 118a, 118b, is provided for detecting a measurement value $S_{measure}$ depending on a currently existing flow parameter of the first and second fluids F1, F2 based on a different physical property of the first and the second fluids F1, F2 in the channel 104. The second feed means 116 is implemented to include an opening 108a to a bottleneck-shaped section of the fluid channel 104 (downstream to the fluid inlet 110). Thus, the second feed means 116 is, in the flow direction of the fluid stream $F_{1-2}$ arranged downstream to the first feed means 114. The second feed means 116 is arranged as an opening 108a, in the channel section for feeding the second fluid F2 (at the bottleneck shaped section of the channel 104) such that, with a (every) diaphragm excursion of the micropump of the first feed means 114, a quantity (e.g. a droplet) of the second fluid F2 is injected into the first fluid F1 in the channel 104 at the inlet 110 so as to form the interface between the first fluid F1 and the second fluid F2.

According to the inventive embodiment of the microfluidic device 200 for detecting a flow parameter as illustrated in FIG. 2b, the second fluid F2 is fed into the first fluid F1 at a bottleneck-shaped section of the fluid channel 104 upstream to the channel inlet 110. Given a first fluid pressure P1 of the first fluid downstream to the bottleneck-shaped fluid channel section, a second pressure value P2 of the first fluid F1 in (approximately) the middle of the bottleneck-shaped section of the fluid channel, and a third pressure value P3 of the second fluid F2 in the reservoir 126, the Bernoulli law applies, as follows, to the above-mentioned pressure values P1, P2 and P3, wherein $v_1$, $v_2$ is the respective fluid flow speed of the first (and the second) fluid(s) F1(F2) at a point on a streamline, and ρ is the respective density of the first and second fluid F1, F2 at all points in the fluid F1, F2:

$$P_1 + \tfrac{1}{2}\rho v_1^2 = P_2 + \tfrac{1}{2}\rho v_2^2$$

Due to the Bernoulli law, the pressure value P2 of the first fluid F1 at the bottleneck-shaped section of the fluid channel falls below the third pressure value P3 of the second fluid F2 at the second inlet 108, if the fluid flow speed of the first fluid F1 is at the bottleneck-shaped section of the fluid channel sufficiently high. Thus, a small quantity of the second fluid F2 (such as, for example, a small droplet) is injected into the stream path with the suction strokes by the micropump of the first feed means 114, if the pressure value P2 of the first fluid F1 at the first inlet 106 (at the bottleneck-shaped section of the fluid channel 104) falls below the third pressure value P3 of the second fluid F2 at the second inlet 108. These small injected quantities of the second fluid F2, exemplarily in the form of droplets, may then, as the subsequent discussion will clearly show, be used for measuring a flow parameter of the fluid stream $F_{1-2}$ within the channel 104. To prevent any unwanted (e.g. gaseous) flow of F1 into the channel 108, it is possible to arrange a hydrophilic filter, wetted by the liquid F2, at the entrance 108a. which cannot be passed by the gas F1.

With regard to the arrangement of the inventive microfluidic device 200 as illustrated in FIGS. 2a-b, it is pointed out that the other optional elements as illustrated in FIG. 1b may equally be used here. In addition, the description illustrated referring to FIGS. 1a and 1b may equally be applied to the alternative microfluidic device 200 illustrated in FIGS. 2a-b.

As shown in FIG. 2a, the first feed means 114 comprising the micropump and the second feed means 116 are arranged at the channel 104 on the input side, wherein the second feed means 116 is arranged, in the flow direction, upstream from the first feed means 114, and the second feed means 116 is arranged, as an opening within the channel 104 for feeding the second fluid F2.

As shown in FIG. 2a, the first feed means 114 comprising the micropump and the second feed means 116 are arranged at the channel 104 on the input side, wherein the second feed means 116 is arranged, in the flow direction, downstream from the first feed means 114, and the second feed means 116 is arranged, as an opening within a narrowed channel section 116 for feeding the second fluid F2.

As shown in FIGS. 2a-b, the first and the second feed means 114, 116 are configured to adjust the pressure P2 of the first fluid F1 in the first inlet 106 and the pressure P3 of the second fluid F2 in the second inlet 106 for injecting a quantity of the second fluid F2 into the channel 104 so as to form the interface between the first fluid F1 and the second fluid F2.

Alternative ways of implementing the inventive microfluidic device 100, 200 for detecting a flow parameter have been presented using the above descriptions of FIGS. 1a, b and 2a-b, wherein the microfluidic device may exemplarily also be referred to as a passive flow sensor.

Further embodiments and specific realizations of microfluidic dosing systems using the above-described inventive microfluidic devices 100, 200 for detecting a flow or dosing parameter shall now be described by means of FIGS. 3-5. As for the further description it shall be noted that all of the elements depicted as optional with regard to FIG. 1b may essentially be equally applied to any of the embodiments depicted below by means of FIGS. 3-5; not all of the optional functional elements depicted in FIGS. 1a-b will be explained once again in detail in the following descriptions of the embodiments.

Figure 3:
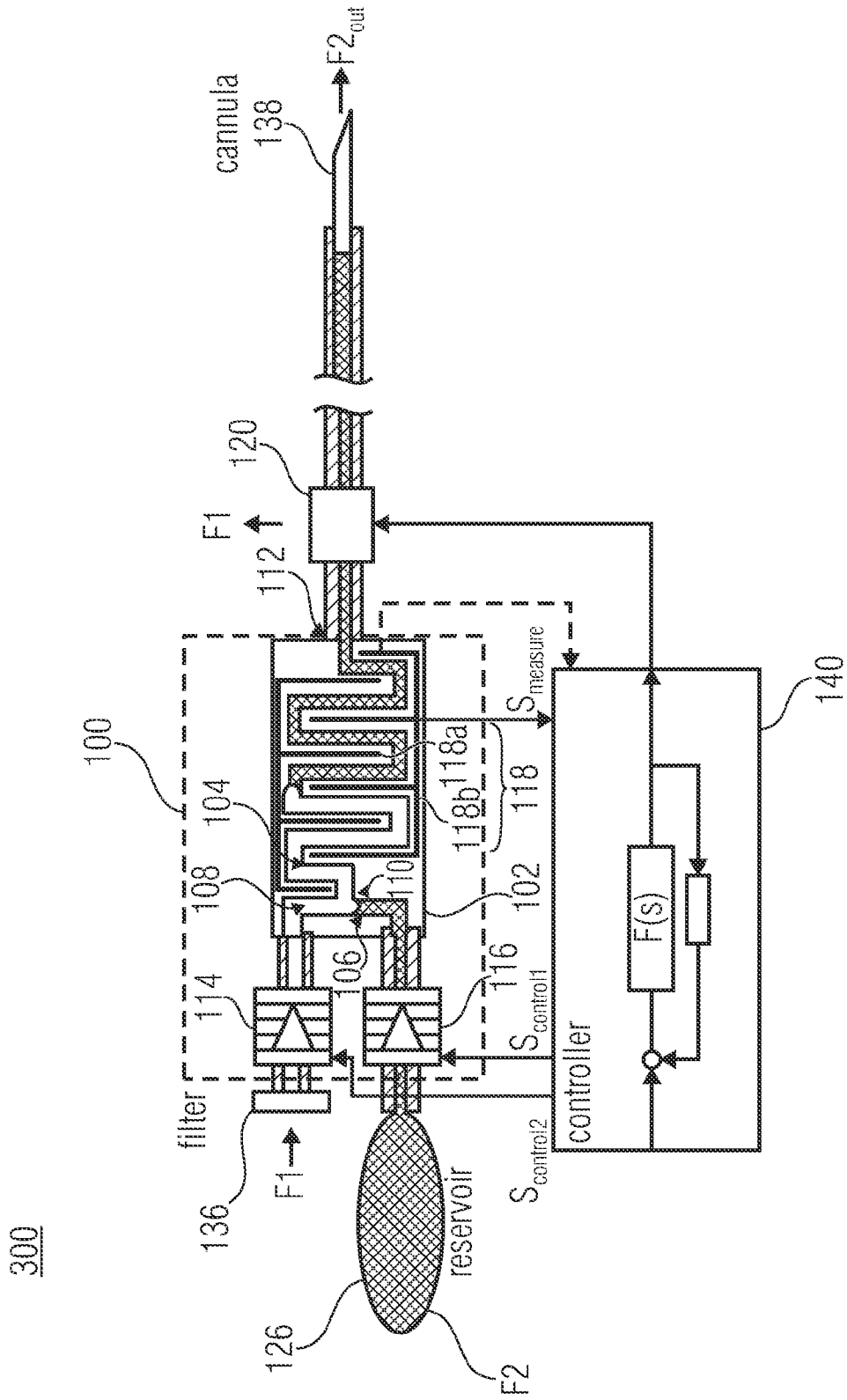
FIG. 3 shows a schematic illustration of a microfluidic dosing system in accordance with another embodiment of the present invention.

FIG. 3 shows a schematic representation of an implementation of a microfluidic dosing system 300 using the microfluidic device 100. As is depicted in FIG. 3, the microfluidic dosing system 300 comprises the microfluidic device 100 for detecting a flow and/or dosing parameter. The microfluidic device 100 again comprises a channel 104 configured within a base body 102. The channel 104 has a first inlet 106 for feeding a first fluid F1 and a second inlet 108 for feeding a second fluid F2 so as to form a fluid stream $F_{1-2}$ comprising the first and second fluids F1, F2 within the channel 104 on the input side, i.e. at the input 110 of the channel 104, and further comprises an output 112 for providing the fluid stream $F_{1-2}$ on the output side. The channel 104 again has cross-sectional dimensioning for configuring, between a section of the channel 104 that is filled with the first fluid F1 and an adjacent section of the channel that is filled with the second fluid F2, a fluid interface between the first and second fluids F1, F2 which extends within the channel 104 over the entire channel cross-section.

In addition, a first feed device 114 having a micropump is arranged which is associated with the first inlet 108 for selectively feeding the first fluid F1 to the channel input 110. The second feed device 116 is associated with the second inlet 108 so as to feed the second fluid F2 to the channel 104 at the channel input 110. Optionally, the second feed device 116 may further comprise a second micropump, but this is not necessarily the case. For example, a reservoir 124 for the second fluid F2, which is arranged at the second feed means 116, may be configured to feed, e.g., a continuous flow of the second fluid F2 to the inlet 106 and, thus, to the channel input 110.

Similarly, the second feed means 116 may have a second micropump associated with it for selectively feeding the second fluid F2 from the reservoir 124 to the channel input 110 via the first inlet 106. As is depicted in FIG. 3, the first inlet 106, the second inlet 108 and the channel input 110 may be configured, for example, as a so-called T-piece, for example; it also being possible, of course, to similarly also provide a channel input 110 configured as a Y hose connection or any other inlet for selectively feeding the first and second fluids F1, F2.

The microfluidic device 100 of the microfluidic dosing system 300 further comprises a detection means 118 for detecting a measurement value $S_{MEASURE}$, which is dependent on a current flow parameter of the first or second fluid F1, F2, on the basis of a different physical property of the first and second fluids F1, F2 within the channel 104. Since said different physical property may be, for example, a different electrical conductivity, a different dielectric conductivity (permittivity), a different magnetic conductivity (permeability), a different optical transparency or a different optical reflectivity of the first fluid F1 and of the second fluid F2, the detection means 118 may be configured, for example, with first and second detection sections 118a, 118b so as to selectively detect the respectively different physical property of the first and second fluids F1, F2.

In addition, the microfluidic dosing system 300 comprises a controller 140, said controller 140 being configured, for example, to detect the measurement value $S_{MEASURE}$ detected by the detection means 118, which measurement value is based on the different physical property of the first and second fluids F1, F2, so as to determine the current flow parameter of the first or second fluid F1, F2 within the channel 104 from one or more positions of one or more fluid interfaces between the first and second fluids F1, F2. Moreover, the controller 140 is configured to selectively control at least the first feed means 114 and (optionally) the second feed means 116 to control feeding the first fluid and/or of the second fluid to the channel input 110 via the respective inlet 106, 108 so as to obtain a predefined flow parameter (set value) of the first and second fluids F1, F2 within the channel 104. Thus, the controller 140 is configured to selectively control at least the first feed means 114 and, optionally, also the second feed means 116 to feed the first and second fluids F1, F2 to the channel input 110 so as to obtain the predefined flow parameter of the fluid stream within the channel 104, it being possible for said control of the first and second feed means 114, 116 to be based, for example, on a deviation of the determined current flow parameter (actual value) from the predefined flow parameter (set value).

FIG. 3 further shows that the first feed means 114 has the first fluid F1, e.g. an ambient gas, provided to it from an environment via a filter element 136, for example. FIG. 3 further depicts that the fluid separation means 120 is configured to separate the first fluid F1 from the fluid stream $F_{1-2}$ within the channel 104 and to release it again to the environment, for example, whereas the output-side fluid stream $F2_{OUT}$ contains the second fluid F2 to as exclusive an extent as possible, for example. If the microfluidic dosing device 300 depicted in FIG. 3 is employed in the field of medicine technology, for example, said dosing device 300 may be configured as a drug dosing means, for example, for administering the fluid F2 containing a drug to a patient via a cannula 138.

Otherwise, the microfluidic device 100, depicted in FIG. 3, of the microfluidic dosing system 300 may comprise any of the functional elements depicted in FIGS. 1a, 1b as well as all of the optional functional elements.

A further inventive embodiment of a microfluidic dosing system 400 will be represented below with reference to FIG. 4. The microfluidic dosing system 400 depicted in FIG. 4 differs from the microfluidic dosing system 300 depicted in FIG. 3 in that the first output 120a of the fluid separation means 120 is fluidically coupled to the first inlet 106 of the fluid channel 104 for providing the first fluid F1 separated from the fluid stream $F_{1-2}$. The fluid F1 separated by the fluid separation means 120 is thus led to the first feed means 114 so as to form, e.g., a closed cycle for the first fluid F1 from the fluid separation means 120 to the first inlet 106 of the fluid channel 104.

Figure 4:
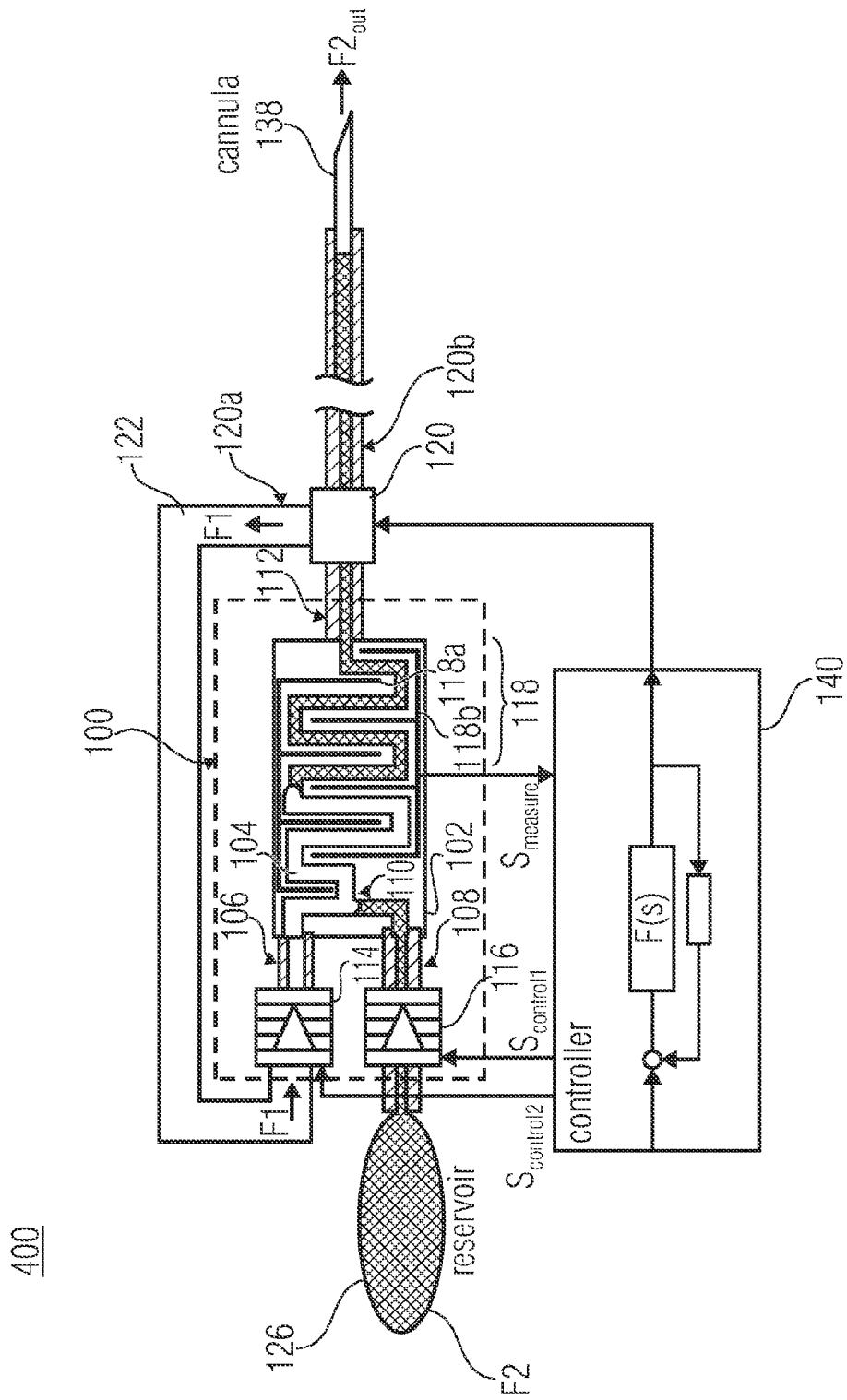
FIG. 4 shows a schematic illustration of a microfluidic dosing system in accordance with another embodiment of the present invention.

Otherwise, the functionality of the inventive microfluidic dosing arrangement 400 depicted in FIG. 4 and of the approaches that are possible as a result in terms of dosed provision of a predefined dosing quantity of the second fluid F2 at the output of the microfluidic dosing system 400 corresponds to the approaches, depicted in FIG. 3, of dosing the second fluid F2.

However, the arrangement represented in FIG. 4 enables a number of further advantages. For example, a negative pressure is created at the first output 120a of the fluid separation means 120 by the first feed means 114 via the fluidic coupling to the first output 120a of the fluid separation means 120 upon activation of the first feed means 120 (for example by the controller 140), so that separation of the first fluid F1 from the fluid stream $F_{1-2}$ provided on the output side of the channel 104 is supported. For example, if the first fluid F1 is a gas, and if the first feed means 114 is designed as a gas pump, gas bubbles may thus be more effectively separated from the fluid stream $F_{1-2}$ by the fluid separation means 120.

Since there is a closed cycle for the first fluid F1, there is, e.g., no risk of contamination for a patient in a medico-technological application, so that no sterile filter in the form of the filter element 136 is necessitated upstream from the first fluid feed means 114. Since the microfluidic dosing system 400 depicted in FIG. 4 necessitates no contact with the surrounding atmospheric pressure since, for example, also the second fluid F2 is provided within the self-contained fluid reservoir 126 of the second feed means 116, said dosing system 400 may also be implanted in a patient, for example.

Since the first fluid F1 within the cycle will be saturated with molecules of the second fluid F2 after a certain amount of time, no second fluid F2 will be absorbed into the first fluid F1 any longer, e.g. it will not mix with the first fluid F1 and it will not evaporate, as a result of which, for example, faulty measurements or inaccuracies may be avoided, since following saturation of the first fluid F1 (with molecules of the second fluid F2), no more undesired "migration" of the fluid interface will take place. For example, if the first fluid F1 is a gas and the second fluid F2 is a liquid drug, the gas within the cycle will be saturated with drug vapor after a certain amount of time, so that no drug can evaporate through the fluid separation means 120 any longer.

As already outlined above, also the second fluid F2 (e.g. a liquid) should be supplied in a manner that it is nearly saturated with molecules of the first fluid F1 (e.g. a gas), so that an evaporation of the second fluid F2 into the first fluid F1 or an dissolving of the first fluid F1 into the second fluid F2 will be minimized. Together with a defined ambient temperature and small exchange area (i.e. cross section of the fluid interface) the exchange between the first fluid F1 and the second fluid F2 will be reduced to a minimum value.

In addition, it is to be noted that the microfluidic dosing system 400 depicted in FIG. 4 may also be configured to be self-adjusting. When the second feed means 116 feeds the second fluid F2, no quantity of the second fluid F2 may travel in the direction of the first inlet 106 for the first fluid F1, since the first inlet 106 of the first fluid feed means 114 is self-contained, or sealed-off, or acts, at the fluid separation means 120, on the excess pressure of the second fluid feed means 116. Thus, due to the sealed-off volume of the first fluid F1, excess pressure would build even if the first feed means for the first fluid F1 had leakage rates. As was already indicated above, the first fluid may be a gas, for example, whereas the second fluid F2 is a liquid or a liquid drug.

Figure 5:
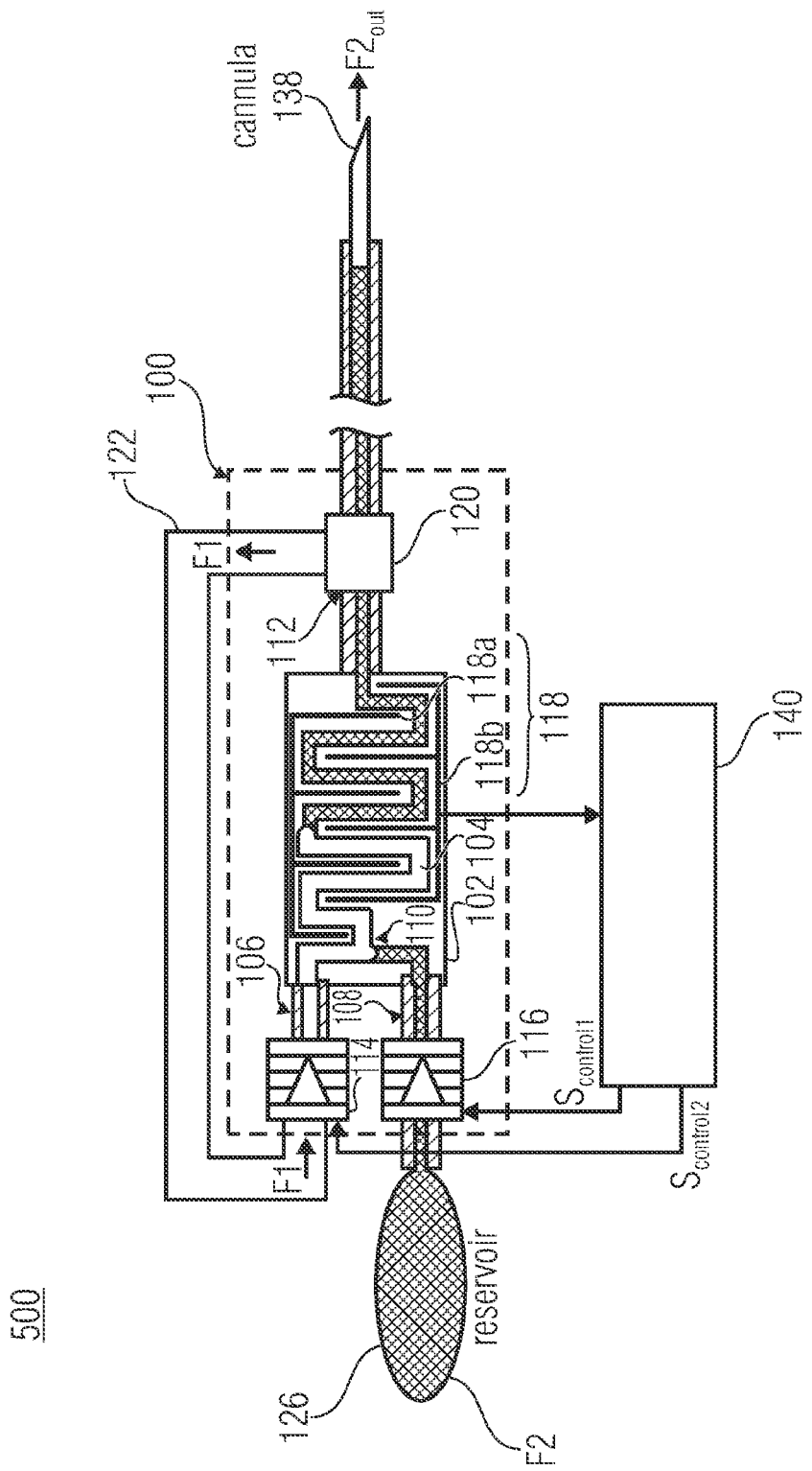
FIG. 5 shows a schematic illustration of a microfluidic dosing system in accordance with another embodiment of the present invention.

FIG. 5 now shows a further schematic representation of an inventive microfluidic dosing system 500 in accordance with a further embodiment of the present invention.

In the microfluidic dosing system 500 depicted in FIG. 5, the fluid separation means 120 is configured immediately downstream from the channel output 112, for example. This arrangement may be achieved, for example, in that the fluid channel 104 (e.g. in the form of a meandering channel) and the fluid separation means 120 are manufactured or integrated within a semiconductor body, e.g. within a silicon material. In this manner, a so-called dead volume—which is not taken into account, e.g., for a volume measurement for dosing the dosing quantity of the second fluid F2—at the channel output 112 may be avoided or minimized.

The fluid separation means 120 may now be designed as illustrated in FIG. 1b, for example. For example, if the first fluid F1 is a gas and the second fluid F2 is a liquid drug or a drug dissolved in a liquid, the fluid separation means 120 may be realized, for example, in the form of a gas-bubble separation chamber having a low chamber height that is configured to be smaller than the diameter of the fluid channel 104. The chamber height may correspond, for example, to 1 to 2 times the value of a cross-sectional dimension (e.g. diameter, lateral length, etc.) of the fluid channel 104. In addition, a hydrophobic (liquid- or water-repellent) filter diaphragm having a small pore diameter is arranged as a demarcation of the chamber. This filter diaphragm is impermeable, for example, for the fluid F2 (in the form of a liquid), i.e. it has a so-called high "bubble point", so that the pores of the filter diaphragm are essentially not wetted by the liquid F2. Due to the low chamber height, the gas (fluid F1) definitely comes into contact with the hydrophobic filter diaphragm. The pore inside the hydrophilic filter membrane are not wetted, as there is only gas inside the pores. The gas to be separated contacts definitely the gas inside the pores, with that the gas bubble can pass through the filter pores immediately without any capillary pressure. The excess pressure within the chamber, which is exerted by the first and second feed means 114 and 116, in combination with the sucking negative pressure across the separation chamber at the first output 120a of the fluid separation means 120, which is exerted by the first fluid feed means 114 thus fluidically coupled thereto, leads to reliable separation of the first fluid F1 from the fluid stream $F_{1-2}$ in the form of the gas bubbles.

It is pointed out that there is a number of design choices for configuring the fluid separation means 120, e.g. with respect to the dimensions of the separation chamber dimensions, the area of the hydrophilic filter membrane, the number of pores per unit area, the pore diameter etc, in order to ensure an essentially complete separation of the first fluid F1 and the second fluid F2, which are fed to the separation means 120 as the fluid stream $F_{1-2}$.

A number of approaches to dosing the second fluid F2 as precisely as possible on the output side of the inventive microfluidic dosing device 300, 400, 500 and/or the outlet of the microfluidic device 100, 200 will now be explained below.

In a first approach, the detection means 118 is configured to detect a position or a change in position of the fluid interface within the channel 104 on the basis of the different physical property of the first and second fluids. The controller 140 is configured to control, on the basis of the measurement value $S_{MEASURE}$ provided by the detection means 118, the first and second feed means 114, 116 such that the second fluid F2 is initially fed into the channel on the input side until an existing fluid interface (with a fluid transition from the first F1 to the second fluid F2 in the fluid stream) is detected at a predefined intermediate position within the channel 104 or at the channel output 112. At this point, feeding of the second fluid F2 to the channel 104 is stopped, so that there is a predefined dosing volume within the channel 104 (up to the intermediate position or to the end position at the channel output 112) which corresponds to the geometric volume of the volume taken up by the second fluid F2 within the channel 104. Thus, there is a defined quantity of the second fluid within the channel 104.

The controller 140 is further configured to control the first feed means 114 to feed the first fluid F1 to the channel, so that the defined quantity of the second fluid F2 is provided as an output-side fluid stream $F2_{OUT}$ at the channel output 112 and/or downstream, in the flow direction, from the fluid separation means 120. Thus, the desired dosing volume may be fed to a patient through the cannula 138, for example. Since the dosing quantity of the second fluid F2 may be defined with extremely high precision, this dosing operation is self-adjusting, the excess first fluid F1 being separated (essentially) completely from the fluid stream $F_{1-2}$ by the fluid separation means 120 and thus not being contained within the output-side fluid stream $F2_{OUT}$. This dosing operation may be repeated any number of times so as to provide the predefined dosing quantity of the second fluid F2 on the output side. If the detection means 118 is configured to detect the fed fluid stream at any intermediate position within the channel 104, any intermediate quantities may be adjusted—from a completely filled channel up to a minimally filled channel comprising a minimum feed quantity of the feed means 116.

The repetition frequency of the previously described first alternative for an inventive dosing operation may now be adjusted so as to adjust the dosing quantity of the second fluid F2 that is provided per time unit at the channel output or at the output of the fluid separation means 120. To this end, the feed velocity of the first and second fluids F1, F2 to the respective inlet 106, 108 to the channel 104 may be adjusted via the controller 140.

Depending on the electrical excitation, the stroke volumes of micromembrane, or microdiaphragm, pumps may exemplarily be varied in a range from 10 nanoliters to 100 microliters per pump process. Thus, an essential advantage of the present microfluidic dosing system consists in that the fluid feed means 114, 116 (e.g. in form of micropumps) may be subject to a certain amount of scattering or to certain inaccuracies when feeding the respective volume packets of the first or second fluids F1, F2, since any intermediate positions of an interface transition between the first and second fluids F1, F2 within the fluid channel 104 and, e.g., at the channel output 112 may be accurately detected with the inventive detection means 118. Thus, corresponding switch-off of the respective feed means 114, 116 may yield a highly accurate dosing volume or a highly accurate dosing volume flow within the fluid channel 104. In this context, it is only necessary for the respective fluid feed means 114, 116, or the micropumps or microdiaphragm pumps used for this purpose to be able to feed sufficiently small increments (e.g. 10 nanoliters to 100 microliters) of fluid quantities of the first and second fluids F1, F2 to the fluid channel 104 so as to be able to achieve the desired dosing quantities within the fluid channel 104 as accurately as possible. Thus, the accuracy requirements placed upon the micropumps or microdiaphragm pumps used are relatively low in the inventive microfluidic dosing system.

Especially the dosing accuracy of micropumps depend on many parameters, e.g. on back pressure, accuracy of the actuation voltage, quality of the glue layer joining the piezo, temperature (viscosity change, thermal expansion of piezo/membrane actuation), humidity as well as especially the presence of gas bubbles inside the pump chamber. One advantage of the inventive microfluidic dosing system is the fact, that the dosing accuracy is independent on these influences, the change of stroke volume of the micropumps, caused by any of these disturbances, can be detected. The effective real pump stroke volume will be measured in a reliable way by the detection means 118.

The geometry (cross section, length) of the channel 104 is well defined and known by the manufacturing process, For that, it shall be noted that the inventive microfluidic dosing system 300, 400, 500, 400, 500 and/or the microfluidic device 100, 200 may also be employed without any calibration operation independent on the fluids F1 and F2, since it is either possible to directly determine a position of a fluid interface within the fluid channel, or it is possible to obtain a defined dosing quantity of the second fluid F2 within the fluid channel 104 by using a stop electrode at any position of the channel 104, advantageously at the channel output 112 (or at any intermediate position along the fluid channel 104). Thus, one important advantage of this approach is that no calibration of the detection means 118 is necessitated.

In an optional alternative of the first approach, the detection means 118 is configured to comprise the start electrode 133 and the stop electrode 134 in order detect a position of the fluid interface at two different positions within the channel 104, e.g. at the channel inlet 110 and the channel outlet 112, on the basis of the different physical property of the first and second fluids.

The controller 140 is configured to control, on the basis of the measurement value $S_{MEASURE}$ provided by the detection means 118, the first and second feed means 114, 116 such that the first fluid F1 (e.g. a gas) is initially fed into the channel on the input side until an existing fluid interface (with a fluid transition from the second fluid F2 to the first fluid F1 in the fluid stream) is detected at a predefined intermediate position within the channel 104 or at the channel output 112 by means of the stop electrode 134, or until the complete channel 104 is filled with the first fluid F1. At this point, feeding of the first fluid F1 to the channel 104 is stopped, so that the channel 104 (up to the intermediate position or to the end position at the channel output 112) is filled with the first fluid F1.

Then, the second fluid F2 is fed into the channel on the input side 110, wherein the start electrode 133 is arranged to detect the feeding of the second fluid F2 into the channel 104. The second fluid F2 is fed into the channel on the input side 110 until an existing fluid interface (with a fluid transition from the first F1 to the second fluid F2 in the fluid stream) is detected at a predefined intermediate position within the channel 104 or at the channel output 112 by means of the stop electrode 134. At this point, feeding of the second fluid F2 to the channel 104 is stopped, so that there is a predefined dosing volume within the channel 104 (up to the intermediate position or to the end position at the channel output 112) which corresponds to the geometric volume of the volume taken up by the second fluid F2 within the channel 104. Thus, there is a defined quantity of the second fluid within the channel 104 (between the positions of the start electrode 133 and the stop electrode 134).

The controller 140 is further configured to control the first feed means 114 to feed the first fluid F1 to the channel 104 which is at least partially filled with the second fluid F2, so that the defined quantity of the second fluid F2 is provided as an output-side fluid stream $F2_{OUT}$ at the channel output 112 and/or downstream, in the flow direction, from the fluid separation means 120. Thus, the desired dosing volume may be fed to a patient through the cannula 138, for example. Since the dosing quantity of the second fluid F2 may be defined with extremely high precision, this dosing operation is self-adjusting, the excess first fluid F1 being separated (essentially) completely from the fluid stream $F_{1-2}$ by the fluid separation means 120 and thus not being contained within the output-side fluid stream $F2_{OUT}$. This dosing operation may be repeated any number of times so as to provide the predefined dosing quantity of the second fluid F2 on the output side. If the detection means 118 is configured to detect the fed fluid stream at any intermediate position within the channel 104, any intermediate quantities may be adjusted—from a completely filled channel up to a minimally filled channel comprising a minimum feed quantity of the feed means 116.

The repetition frequency of the previously described optional alternative for an inventive dosing operation may now be adjusted so as to adjust the dosing quantity of the second fluid F2 that is provided per time unit at the channel output or at the output of the fluid separation means 120. To this end, the feed velocity of the first and second fluids F1, F2 to the respective inlet 106, 108 to the channel 104 may be adjusted via the controller 140.

A further alternative approach to dosing a predefined dosing quantity of the second fluid at the output of the microfluidic dosing device 300, 400, 500 and/or the microfluidic device 100, 200 shall be illustrated below.

The controller 140 may be configured to control the first feed means 114 to feed a predefined quantity of the first fluid F1 into a continuous stream of the second fluid F2 that is present at the channel 104 on the input side. In this context, the flow velocity of the second fluid F2 within the channel 104 may be essentially uniform (constant), or it may be adjustable (variable), e.g. in accordance to the controlled operation of the second fluid feed means 116.

With this depicted approach to dosing the dosing quantity of the second fluid F2, for example, a very small increment of the first fluid in the range of several nanoliters (e.g. between 1 and 100 nanoliters) is fed to the adjustable, continuous flow of the second fluid F2 into the channel input 110 on the input side. For example, a very small gas increment may be fed, as the first fluid F1, to a liquid stream as the second fluid F2. Since the flow velocity of said minute quantities (increments) of the first fluid F1 that are fed, e.g., in the form of gas bubbles, corresponds to the flow velocity of the second fluid, the throughput and, thus, the dosing quantity of the second fluid F2 may be determined by detecting the points in time when the increments of the first fluid F1 flow past the respective electrodes of the detection means 118, which are arranged such that they are distributed along the channel, for example.

In addition, the second feed means 116 for feeding the second fluid F2 to the channel input 110 may be controlled by the controller 140 to provide the desired flow velocity and, thus, the desired dosing quantity of the second fluid at the channel output, or on the output side at the fluid separation means 120. The fluid separation means 120, in turn, is operative to remove the first fluid F1 from the fluid stream $F_{1-2}$, so that essentially exclusively the second fluid F2 is provided on the output side per time unit at a predefined flow velocity and, thus, dosing quantity. Depending on the number and size of the individual sensors of the detection means 118 that are arranged at the channel, the accuracy of spatial resolution and, thus, the accuracy of dosing resolution results with respect to the flow velocity of the second fluid F2 to be determined within the channel 104.

If, in the microfluidic dosing system, the individual sensors of the detection means 118 are arranged as an electrode or sensor array along the channel 104, the fluid stream $F_{1-2}$ that is still located within the channel 104, the first fluid F1 and of the second fluid F2 may be continuously monitored. In this context it is not necessitated, for example, to know the exact physical property of the first and second fluids F1, F2 (e.g. the exact permittivity $\in_{r1}, \in_{r2}$) since only a detectable difference in the physical properties of the first and second fluids F1 and F2 have to exist in order to perform a propagation-time detection of minute quantities of the first fluid F1 that are added to the second fluid F2. Thus, it is not necessitated to pre-calibrate the inventive microfluidic dosing system.

In accordance with a further alternative of an approach to adjusting the dosing quantities of the second fluid F2, the previously described detection means 118, which is arranged, e.g., as a sensor array along the channel 104, may again be used. With suitably fine structuring of the detection means 118, i.e. a suitably dense arrangement of the individual sensors along the channel 104, as a result of which a sequentially monitored electrode array is obtained, it is possible to detect both the velocity and the direction of movement of a fluid interface within the channel and, in addition, the size of a fluid section and, thus, the fluid volume or the fluid quantity within the channel 104. The controller 140 may be configured to generate a continuous mixture of the first fluid F1 and of the second fluid F2 as the fluid stream $F_{1-2}$ within the fluid channel, the respective proportion of the first and second fluids F1, F2 and the fluid stream velocity within the channel 104 being adjustable by suitably driving the first and second feed means 114, 116 by means of the controller 140. Thus, highly exact and reliable dosing of the dosing quantity of the second fluid F2 as the output-side fluid stream $F2_{OUT}$ may be obtained.

With regard to the liquid reservoir 124 for the second fluid F2 that is provided in FIGS. 1b, 3 to 5, it shall be noted that said reservoir may essentially be designed to have any size desired, and that thus, the fluid F2 may be provided with a very high dosing accuracy at the output of the inventive microfluidic dosing system in a dosed manner over a relatively long period. In this context, almost any measurement accuracy desired is achievable, depending on the diameter of the fluid channel 104 and on the geometry of the fluid channel 104.

Some general aspects of the present invention will be addressed below which are essentially equally applicable to any of the previously described embodiments.

The above description of the inventive embodiments referred, for example, to that the first fluid F1 is gaseous, e.g. is present as ambient air, whereas the second fluid F2 is a liquid; gas quantities or gas bubbles (fluid F1) having specifically been generated, for example, by the first feed means 114 within the liquid (fluid F2) at the channel input 110. Of course, this approach is equally applicable when the first fluid F1 is a liquid and the second fluid F2 is a gas or air. Thus, for example, the first fluid feed means 114, which in this case is configured as a liquid pump, may generate one or more droplets of liquid and introduce them into a gas stream fed in by the second fluid feed means 116. Finally, the movement of the droplets of liquid within the fluid channel 104 may be detected by the detection means 118, or by the detection means 118 configured as a sensor array. Here, the separation filter diaphragm has to be hydrophilic with small pore size and wetted with the liquid. With that at the separation 120 the liquid contacts to the liquid inside the pores of the hydrophilic filter membrane, and can pass through the filter without capillary pressure losses. The gas fluid F2 can not pass through the wetted pore of the hydrophilic filter and move as desired through the outlet. Therefore, the present inventive concept is equally applicable to dosing minute quantities of air and of gas.

When the inventive microfluidic dosing system 300, 400, 500 comprising the microfluidic device 100 is used, for example, for accurate dosing of minute quantities of air or gas, e.g. of technical gases, it is only necessitated, for example, to replace the hydrophobic (liquid- or water-repellent) diaphragm by a hydrophilic (liquid- or water-attracting) diaphragm within the fluid separation means 120, which means that the fluid separation means 120 may be configured as a liquid separation means, for example. The closed-cycle gas flow, depicted by means of the embodiments of FIGS. 4 and 5, of the first fluid F1 from the fluid separation means 120 to the first fluid feed means 114 is thus replaced by a closed-cycle liquid flow of a suitable liquid (as the first fluid F1). The gas to be dosed (or the second fluid F2) may now be handled in accordance with the above approaches to detecting, evaluating and monitoring the fluid stream $F_{1-2}$ within the fluid channel 104 in that the first fluid F1, which is present as a liquid, is added to or dosed into the second fluid F2 that is to be dosed and is present as a gas, and in that corresponding gas/liquid interfaces (menisci) are created within the fluid channel 104.

In this context it shall be noted that the detection means 118 comprises, e.g., a plurality of individual sensor elements along the fluid channel 104 that are configured to detect the different physical property of the first and second fluids F1, F2 in a spatially resolved manner at a plurality of positions along the channel that are assigned to the individual sensor elements. By means of the selected number, size and distribution of the sensors per length section of the fluid channel 104, the resolution accuracy may be adjusted with regard to the detected positions of the first and second fluids and to corresponding fluid interfaces within the fluid channel. The detection means 118 may be configured as a so-called electrode or sensor array, for example.

The detection means 118 may further be configured to detect whether a fluid interface created at the channel input 110 (e.g. over the entire channel cross-section of the fluid channel 104) is present at all at any intermediate position along the channel 104, or is located directly at the output 112.

Alternatively, an additional detection means 134 (cf. FIG. 1b) may be arranged at the output 112 of the channel, and a further detection means 133 may be arranged at the input of the channel 112, respectively, (or at any intermediate position of the channel 104) so as to reliably detect generation of a fluid interface at the channel input 110 and/or the presence of a fluid interface at the channel output 112 (or at any intermediate position of the channel 104). If, e.g., the detection means 118 or the further detection means 133, 134 do not provide any corresponding measurement signal stating that at a predefined point in time a corresponding fluid interface transition is present at the channel input 110 or channel output 112, the controller 140 may be configured to output a corresponding error signal for communicating this detected state. In addition, safety electrodes 130, 132 may be arranged at the respective feed lines or inlets 106, 108 of the channel input 110, i.e. at the feed lines of the channel input configured as a T-piece, for example, which safety electrodes 130, 132 may detect whether, for example, the first fluid F1 accidentally flows into the second inlet 108 against the flow direction of the second fluid F2 and/or whether the second fluid F2 accidentally flows into the first inlet 106 against the flow direction of the first fluid F1. Should such a "state of disturbance" of the first or second fluid be detected by the additional detection means 130, 132, the controller 140 may further be configured to provide a corresponding error signal in this case, too.

Furthermore, in case of an accidentally flow detected in a quantitative way by 130 (or 132, respectively), the corresponding feed means 114 (or 116, respectively) can be activated by the controller, to push back or to stabilize the accidentally moving meniscus. With that, even in this error case the system can try to compensate the error generating to a more robust and error tolerant behaviour.

In accordance with a further implementation, it is also possible for a further detection means 128 to be arranged at the second output section 120b of the fluid separation means 120, said detection means 128 being configured as a safety electrode, for example, so as to detect whether a quantity of the first fluid F1 that was not able to be separated within the fluid separation means 120 is present within the output-side fluid stream $F2_{OUT}$. If this is so, the controller 140 may be configured, for example, to output a corresponding error signal or a failure alarm. The additional detection means 128 arranged at the second output 120b of the fluid separation means 120 may be configured, for example, to also detect (in accordance with the functionality of the detection means 118) the quantity of the fluid F1 passing through the second output 120b of the separation means 120, it being possible for the controller 140 to be configured to decide whether or not this "disturbance quantity" of the fluid F1 within the output-side fluid stream $F2_{OUT}$ exceeds a threshold value (e.g. in case of drug delivery systems very small quantities of gas bubbles can be accepted to enter the body, but large quantities might be lethal). The detection means 128 effectively has the function of a gas bubble sensor, which is a safety feature in drug delivery systems, or needed at lab-on-chip or analysis systems, if it has to be ensured that no gas bubble enters the system or a biosensor, etc. For example, if a threshold value is exceeded, the controller 140 may be configured to output an error signal. In addition, the controller may be configured to stop the entire microfluidic dosing system so as to abort the dosing operation.

This approach may be necessitated, for example, when the inventive microfluidic dosing system is employed in the field of medical technology. In this manner, one avoids that a gas bubble (as the first fluid F1) is still present within the output-side fluid stream $F2_{OUT}$ of the drug to be dosed; when a gas bubble is determined or a threshold value of the proportion of the gaseous first fluid F1 is exceeded, a failure alarm will be triggered, and optionally, the system will be stopped so as to prevent a health hazard for a patient to be treated with the liquid drug.

As was already mentioned above, a micropump or micro diaphragm pump may be employed for the first feed means 114 and (optionally) for the second feed means 116 so as to feed the first and/or second fluids F1, F2 to the respective inlets 106, 108 and to the channel input 110. The micro diaphragm pumps may be used as piezo-driven micropumps, for example, the maximum stroke volume of which may be adjusted via a maximum control signal, for example. In addition, intermediate stroke volumes may be generated, for example, in that the control signal of the micropump is reduced accordingly, e.g. half a stroke volume for half a control signal, etc. Typical dosing volumes or stroke volumes for one volume stroke are in a range 10 nanoliters to 100 microliters or from 40 nanoliters to 20 microliters, for example.

It shall be noted in this context that an essential advantage of the present microfluidic dosing system consists in that the fluid feed means 114, 116 used or the micropumps used may be subject to a certain amount of scattering or to certain inaccuracies when feeding the respective volume packets of the first and second fluids F1, F2, since any intermediate positions of an interface transition between the first and second fluids F1, F2 within the fluid channel 104 and, e.g., at the channel output 112 may be accurately detected with the inventive detection means 118. Thus, corresponding switch-off of the respective feed means 114, 116 may yield a highly accurate dosing volume or a highly accurate dosing volume flow within the fluid channel 104. In this context, it is only necessitated for the respective fluid feed means 114, 116, or the micropumps or micro diaphragm pumps used for this purpose to be able to feed sufficiently small increments of fluid quantities of the first and second fluids F1, F2 to the fluid channel 104 so as to be able to achieve the desired dosing quantities within the fluid channel 104 as accurately as possible. Thus, the accuracy requirements placed upon the micropumps or micro diaphragm pumps used are relatively low in the inventive microfluidic dosing system.

In addition, it shall be noted that the inventive microfluidic dosing system 300, 400, 500 may also be employed without any calibration operation, since it is either possible to directly determine a position of a fluid interface within the fluid channel, or it is possible to obtain a defined dosing quantity of the second fluid F2 within the fluid channel 104 by using a "start" electrode 133 (i.e. the further detection means 133 at the channel inlet 110) and/or a "stop" electrode 134 (i.e. the further detection means 134 at the channel output 112).

In addition it is to be noted that for example for capacitive detection of a fluid interface within the channel 104, the capacitance value depending on the first and second fluids F1, F2 will change (decrease or increase) for such time until an extreme value (maximum or minimum value) is achieved, said extreme value then indicating complete filling of the channel 104 with the first or second fluid F1, F2, and, thus, a desired dosing quantity then being adjustable within the channel 104. The capacitance value detected will change step by step in accordance with the respective filling of the channel 104 with the first or second fluid F1, F2 as long as the first and second fluids have different dielectric conductivities (permittivities).

Another advantage of the inventive concept is that the inventive microfluidic dosing system 300, 400, 500 and/or the microfluidic device 100, 200 used for this and configured to detect a flow and/or dosing parameter of a first or second fluid F1, F2 may be implemented as a passive sensor, e.g. by being integrated in a semiconductor chip. In particular, the microfluidic dosing system—above all the detection means and/or the sensor array or the capacitive electrode array—may be produced by means of microsystems technology.

FIGS. 6a-d now show a schematic representation of a meander-shaped fluid channel 4 and the detection means 118 together with the sensing electrodes 118a, 118b in accordance with the embodiments of the present invention. In the microfluidic dosing system depicted in FIGS. 6a-d, the detection means 118 having the sensing electrodes 118a, 118b are arranged for performing a capacitive detection principle.

In this connection, it is pointed out to the fact that the arrangements of the detecting electrodes 118a, 118b of the detection means 118, as illustrated above with respect to the different inventive embodiments, is intended only to principally indicate the presence of two (opposing) sensing electrodes 118a, 118b with respect to the fluid channel 104. In order to emphasize the inventive detection principle, FIGS. 6a-d show a cross-sectional view of a meander-shaped fluid channel 104 and the associated sensing electrodes 118a, 118b of the detection means for performing a capacitive detection principle.

For this purpose, the two electrodes 118a, 118b are deposited on the base body 102 such that an electric field, which may be generated between the two electrically insulated electrodes 118a, 118b, extends both in a first section 104b of the fluid channel 104 filled with the second fluid F2 and in a second section 104a of the fluid channel 104 filled with the first fluid, so that a change in the position of the fluid interface 104c leads to a proportional change in capacitance due to the different related permeability of the first and second fluid F1, F2 in the fluid channel 104. Depending on the implementation of the electrodes 118a, 118b, of the channel cross-section and of the design of the channel, a linear relation may be achieved between the change in capacitance and the change in the part of the fluid interface 104c.

As an alternative option, the first and second electrodes 118a, 118b may each consist of a plurality of individual electrodes 118a-1, 118b-1 such that a plurality of individual capacitances is formed between the first and second electrodes 118a-1, 118b-1, wherein these individual capacitances may be read out and detected independently of one another, and additionally a respective predetermined position in the channel 104 may be associated to a single capacitance value determined. Thus, the plurality of individual electrodes 118a-1, 118b-1 may form a sensor array along the fluid channel 104.

Moreover, as a further alternative option, one (e.g. the first or any further) pair of the plurality of individual electrodes 118a-1, 118b-1 (133', 133") may form the start electrode 133, wherein one (e.g. the last or any previous) pair of the plurality of individual electrodes 118a-2, 118b-2 (134', 134") may form the stop electrode 134, so that a pair of individual capacitances is formed between the first pair of electrodes 133', 133" and second pair of electrodes 134', 134" wherein these individual capacitances may be read out and detected independently of one another, and additionally a respective predetermined position in the channel 104 may be associated to a single capacitance value determined. Thus, the two detecting electrodes 118a, 118b of the detection means 118 may be configured to (exclusively) form the start and stop electrode 133, 134.

Figure 6A:
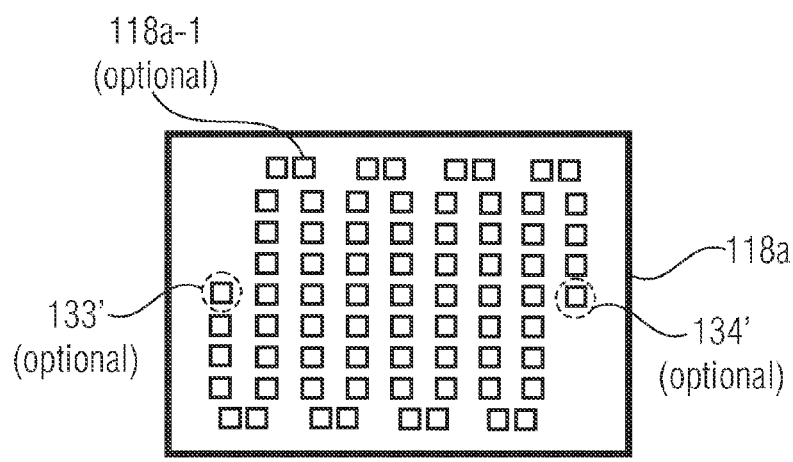
FIGS. 6a-d show a schematic illustration of the arrangement of the two electrodes of the detection means for a capacitive detection of the flow parameter in accordance with another embodiment of the present invention.
Figure 6B:
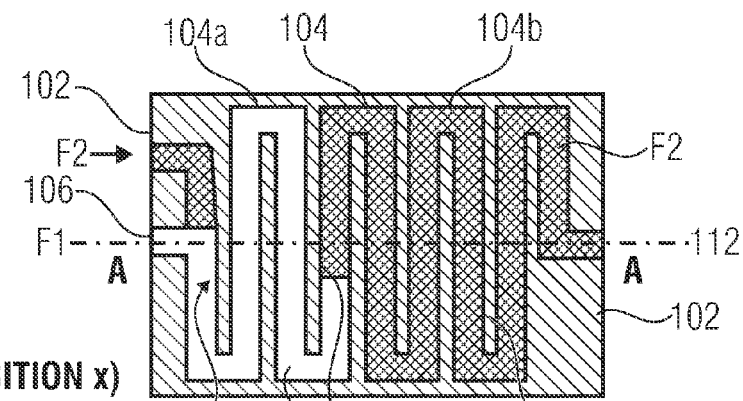
Figure 6C:
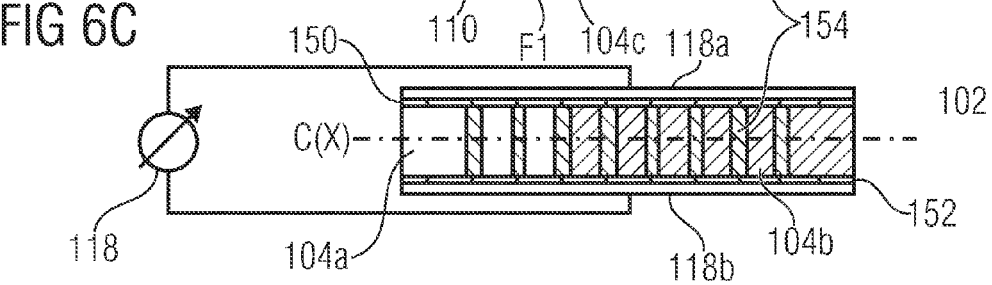
Figure 6D:
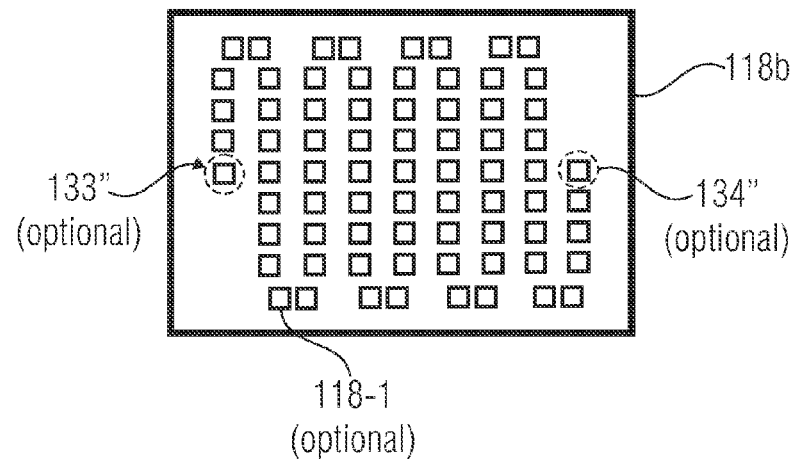

FIG. 6c shows a cross-section through the base body 102 with the fluid channel 104 along line AA of FIG. 6b. The inventive microfluidic device for detecting a flow parameter includes the first sensing electrode 118a, which is also referred to as cap electrode, as well as the other sensing electrode 118b, which is also referred to as bottom electrode. In addition, the channel 104 is represented by the first and second section 104a and 104b, filled with the first and second fluid F1, F2, respectively. The meander-shape of the channel 104 is expressed by ridges 154 of the base body 102, which separated the individual channel sections from each other. As shown in FIG. 6c, the electrodes 118a, 118b are insulated from the channel 104 by insulating layers 152, 154, respectively. The insulating layers are necessitated if the first or second fluid F1, F2 is electrically conductive. If, however, the first and the second fluids F1, F2 are both electrically insulating anyway, the insulating layers 150, 152 may be omitted, wherein the top and bottom electrodes 118a, 118b may directly border to the channel 104.

Finally, the microfluidic device for detecting a flow parameter includes the detection means 118, which are capacitance measuring means, for example. Depending on the position x of the fluid interface 104c in relation to the channel 104, a position-dependent capacitance value C(x) is measured by the detection means 118.

Figure 7A:
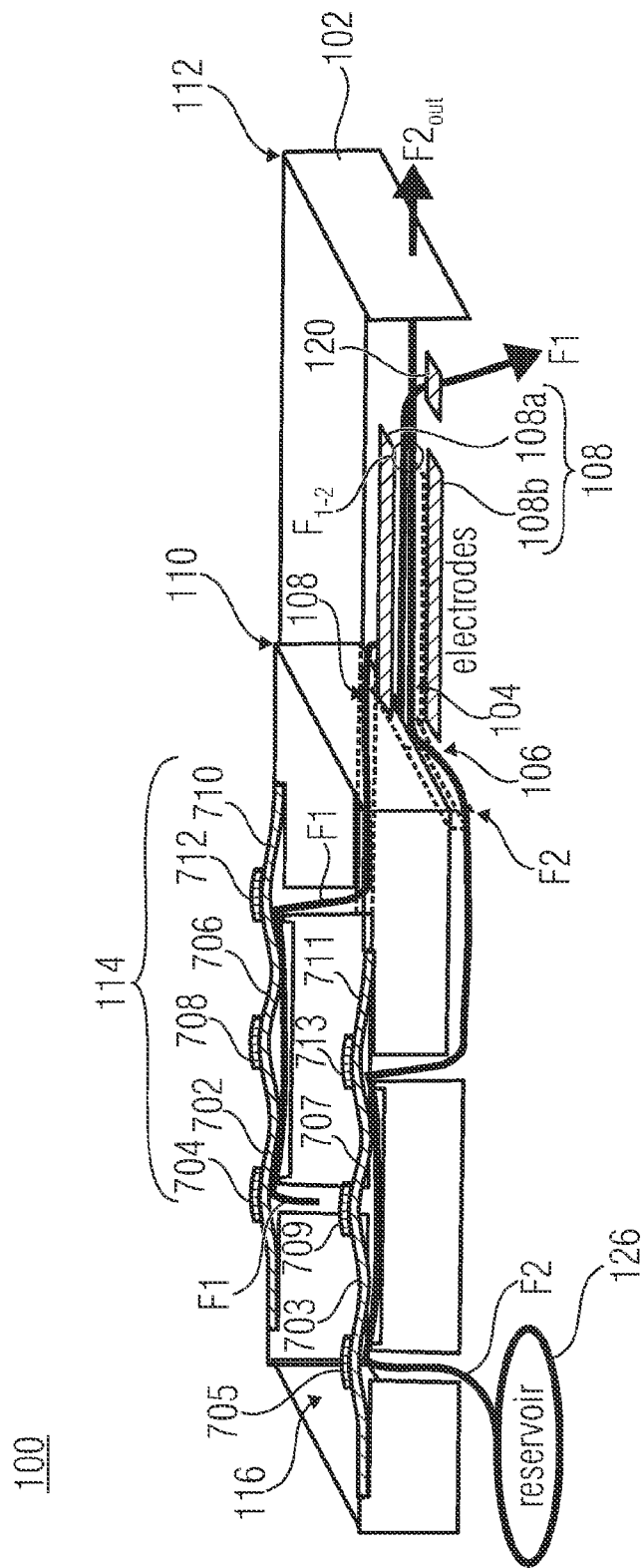

FIGS. 7a-c show different schematic representations of an exemplary implementation of a microfluidic device 100 utilizing so-called peristaltic micropumps as the first and second fluid feed means 114, 116. As outlined above, the inventive approaches to precisely dosing the first and/or second fluid F1, F2 on the output side of the inventive microfluidic dosing device thus impose only relatively weak requirements to the accuracy of the utilized micropumps or microdiaphragm pumps, so that peristaltic pumps can be used as the first and second feed means 114, 116. Based on FIGS. 7a-d, some exemplary implementations of peristaltic pumps 114, 116, which can be advantageously used with the inventive dosing system will now be discussed.

FIG. 7a shows a first and a second peristaltic micropump 114, 116 on a base body 102, each having a first membrane region 702; 703 with a first piezo-actuator 704; 705 for actuating the first membrane region 702; 703, a second membrane region 706; 707 with a second piezo-actuator 708; 709 for actuating the second membrane region 706; 707, a third membrane region 710; 711 with a third piezo-actuator 712; 713 for actuating the third membrane region 710; 711, and a pump body 716.

For the first peristaltic micropump 114 the pump body 716 forms, together with the first membrane region 702, a first valve whose passage opening is open in the non-actuated state of the first membrane region 702 and whose passage opening may be closed by actuating the first membrane region 702. The pump body 716 forms, together with the second membrane region 706, a pumping chamber whose volume may be decreased by actuating the second membrane region 706. The pump body 716 forms, together with the third membrane region 710, a second valve whose passage opening is open in the non-actuated state of the third membrane region and whose passage opening may be closed by actuating the third membrane region 710, wherein the first and second valves are fluidically connected to the pumping chamber.

For the second peristaltic micropump 116 the pump body 716 forms, together with the first membrane region 703, a first valve whose passage opening is open in the non-actuated state of the first membrane region 703 and whose passage opening may be closed by actuating the first membrane region 703. The pump body 716 forms, together with the second membrane region 707, a pumping chamber whose volume may be decreased by actuating the second membrane region 707. The pump body 716 forms, together with the third membrane region 711, a second valve whose passage opening is open in the non-actuated state of the third membrane region and whose passage opening may be closed by actuating the third membrane region 711, wherein the first and second valves are fluidically connected to the pumping chamber.

At the first and second peristaltic micropumps 114, 116, the respective first and second valves are open in the non-actuated state, wherein the respective first and second valves may be closed by moving the membrane towards the pump body, whereas the volume of the respective pumping chamber may be decreased by moving the respective second membrane region also towards the pump body 716. Thus, the peristaltic pumps 114, 116 are normally open, so that (optionally) a safety valve or a different free-flow stop (not shown in FIG. 7a) can be integrated.

Through this construction, the peristaltic micropump enables the realization of bubble-tolerant, self-priming pumps, even if piezo-elements arranged on the membrane are used as piezo-actuator.

In order to ensure that the peristaltic micropump 114, 116 can work in a bubble-tolerant and self-priming manner, it is advantageously dimensioned such that the ratio of stroke volume and dead volume is greater than the ratio of delivery pressure (feed pressure) and atmospheric pressure, wherein the stroke volume is the volume displaceable by the pumping membrane, the dead volume is the volume remaining between inlet opening and outlet opening of the micropump, when the pumping membrane is actuated and one of the valves is closed and one is open, the atmospheric pressure is a maximum of about 1050 hPa (worst case consideration), and the delivery pressure is the pressure necessitated in the fluid chamber region of the micropump, i.e. in the pressure chamber, to move a first/second fluid (liquid/gas) interface past a place representing a flow constriction (bottleneck) in the microperistaltic pump, i.e. between the pumping chamber and the passage opening of the first or the second valve, including this passage opening.

If the ratio of stroke volume and dead volume, which may be referred to as compression ratio, satisfies the above condition, it is ensured that the peristaltic micropump works in a bubble-tolerant and self-priming manner. This applies for both employment of the peristaltic micropump 114, 116 for conveying fluids, when a gas bubble, normally an air bubble, reaches the fluid region of the pump, and the employment of the micropump as a gas pump, when moisture unintentionally condenses from the gas to be conveyed, and thus a gas/liquid interface may occur in the fluid region of the pump.

A further increase of the compression ratio of an peristaltic micropump 114, 116 may be achieved by adapting the contour of a pumping chamber structured in the pump body to the bend line of the pumping membrane, i.e. the bend contour thereof in the actuated state, so that the pumping membrane may substantially displace the entire volume of the pumping chamber in the actuated state. Furthermore, the contours of valve chambers formed in the pump body may also be correspondingly adapted to the bend line of the respective opposing membrane sections, so that in the optimum case the actuated membrane region substantially displaces the entire valve chamber volume in the closed state.

However, it has to be noted that, in order to cause an upward movement of the membrane, a negative voltage, i.e. a voltage opposing the polarization direction, would have to be applied to the piezo-ceramic. However, this would lead to a depolarization of the piezo-ceramic already at low field strength in opposite direction.

The following evaluations are equally applicable to any combination of the piezo-actuator (704, 708, 712; 705, 709, 713) and the associated actuator-membrane (702, 706, 710; 703, 707, 711) as shown in FIG. 7a.

Thus, in order to realize an upward movement of the membrane, i.e. in direction of the piezo-ceramic, and to maximize the compression ratio, a pre-bulged pump membrane is provided, which is adapted to the piezo membrane movement or, in general, to the actuator-membrane movement. To achieve a pre-bulging of the pump membrane that is adapted to the movement of the pump membrane caused by the piezo-actuator (704, 708, 712; 705, 709, 713) bonded to the pump membrane (702, 706, 710; 703, 707, 711). The piezo-actuators are bonded to the pump membrane such that the pump membrane assumes a pre-bulged shape when the piezo-actuator is not actuated. Thus, when the piezo-actuator is actuated, and correspondingly the membrane to assume the second less-bulged position, the tension or stress of the pump membrane caused by the piezo-actuator in the non-actuated state is reduced. The piezo-actuator can, for example, be bonded to the pump membrane when both have a planar shape. Due to the different temperature coefficients and/or the application of a production signal to contract the piezo-actuator laterally when bonding the piezo-actuator to the pump membrane, the pump membrane together with the piezo-actuator assumes an upwardly pre-bulged shape in the first bulged position when the piezo-actuator is not actuated. The actuation of the piezo-actuator causes the piezo-actuator to contract again (at the same time reducing the tension of the pump membrane), the downward deflection of the membrane representing the reverse deflection to the pre-bulging, and in case the drive signal for driving or actuating the piezo-actuator is strong enough to cause the piezo-actuator to assume again the planar or an least essentially planar shape without or at least negligible bulges at the border.

In other words, the deformation of the membrane caused by the actuation of the piezo-actuator represents the inverse effect and deformation caused by the pre-bulging and, thus, at least reduces the bulges or deflections at the borders of the pump membrane.

According to the described peristaltic micropumps, the bending shape of the pre-bulged pump membrane is adapted to the deformation caused by the actuation of the piezo-actuator, such that the pump membrane facing the pump body has a planar base shape when the pump membrane is in the second less bulged or planar position and no counter-pressure is applied. The term "planar base shape" indicates that in case the pump chamber floor is planar or planar with cavities, the pump membrane has a planar shape, and in case the pump chamber floor or the pump membrane comprise protrusions as anti-sticking means distributed over the pump chamber floor, the pump membrane may be slightly bulged at the border of the pump chamber floor, where the outmost anti-sticking means are arranged and assumes there from towards the central part of the pump chamber a planar shape carried by the anti-sticking protrusions due to its stiffness.

According to the present micropump, the piezo-actuator is connected to the pump membrane in a contracted state, i.e. a predetermined production signal or voltage is applied to the piezo-actuator to cause the contraction of the piezo-actuator, and the signal voltage is released afterwards. Due to the release of the signal or voltage, the piezo-actuator extracts and thus bends the membrane together with the drive means upwards and away from the pump chamber. Therefore, the described peristaltic micropumps have a self-priming behavior, and are suitable for conveying compressible media like gasses and are, in addition, bubble-tolerant and bubble independent.

The peristaltic Micropumps are considered bubble tolerant when they are adapted such that if a bubble is entering the pump chamber the micropump is still working, and the bubble (or a part of the bubble) will be transported through the pump chamber. However, the pump rate can be changed, during the presence of the gas bubble (or parts of them) in the pump chamber. Micro pumps are considered bubble independent when they are adapted such that if a bubble is entering the pump chamber, the micropump is not only still working, but the pump rate is independent of the presence of gas in the pump chamber.

Alternatively, as shown in FIG. 7b, a ridge 720, 722 may be provided in the respective valve chamber in the region of the largest stroke of the membrane section, which is correspondingly shaped so as to be able to be completely sealed by the bend of the membrane section. More specifically, the ridge 720, 722 bends upward toward the edges of the valve chamber.

As shown in FIG. 7c, a microfluidic device 100 with four fluid chambers C1-C4 may for example form a branch structure or a mixer, in which the mixing flows $F_{1-2}$ may actively be conveyed. The expansion to four fluid chambers C1-C4 with four associated fluid actuators enables, as it is for example shown in FIG. 7c, the realization of two peristaltic pumps 114, 116. With this, it is possible that a separate piezo-actuator (704, 708, 712; 705) is provided for each fluid chamber C1-C4. Thus, the entire fluidics may be designed very flat, wherein the functional, fluidic structures including fluid chambers C1-C4, channels 104, membranes (702, 706, 710; 703), piezo-actuators (704, 708, 712; 705), and supporting structures 102 may have an overall height on the order of 100 to 500 µm. Thus, systems are possible, which may be integrated in chip cards. Furthermore, even flexible fluidic systems (e.g. made of structured foil layers) are possible. A further possible application of the inventive microfluidic device 100 is a "insulin patch pump" with integrated dosing control, as insulin dosing plaster with integrated dosing monitoring.

Some further general aspects of the present invention with respect to FIG. 7a-c will be addressed below, which are, however, essentially equally applicable to any of the previously described embodiments.

As shown in FIGS. 7a-c, an injection-molded part or injection-embossed part can be used which has both peristaltic pumps realized on one side thereof, and has the T-piece, the electrodes, meanders and bubble separator realized on the other side thereof.

An advantage of the pre-tensioned actuators (piezo-actuators) is that it is not necessitated to cover the pumping chambers and valve chambers with expensive injection molding dies. The high planar quality of the surface of the body is defined by the initial material and may not be manufactured during injection moulding and/or embossing. The pumping chamber floor may be realized as a flat plane, wherein the sealing lip or ridge possibly protrudes slightly (e.g. 3 to 30 or about 10 µm). Moreover, a soft sealing film may be used to improve the tightness of the active valves.

The microfluidic device 100 shown in FIG. 7c provides some further advantages. The microfluidic device comprises four instead of six piezo-ceramics (piezo-actuators, see FIG. 7a), wherein all of the channels are on a top side of a low-cost fluidic chip 102. Moreover, simple and inexpensive fabrication process can be realized. The pre-tensioned diaphragm is advantageously made of stainless steel, and is glued onto the cap/cover film. The reservoir 126 may comprise an elastic wall so that no negative pressure arises during emptying, and optionally has a septum and/or an inlet port for filling (not illustrated).

Figure 8:
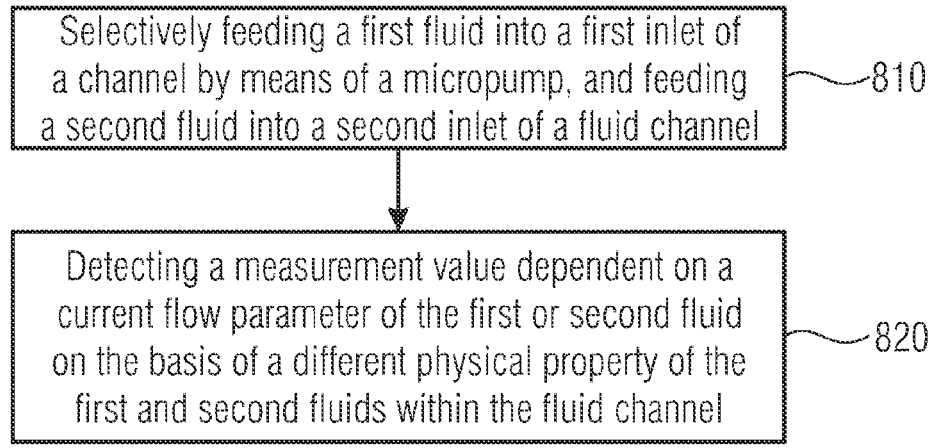
FIG. 8 shows a flow chart of a method for detecting a flow parameter in accordance with another embodiment of the present invention.
Figure 9:
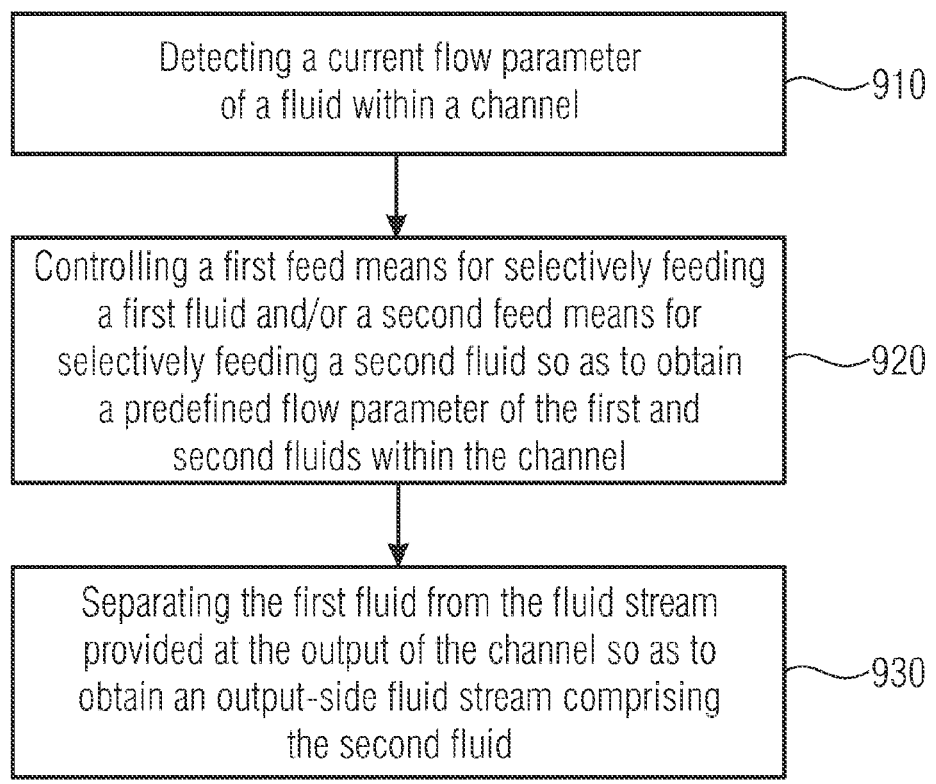
FIG. 9 shows a flow chart of a method for microfluidically dosing a fluid in accordance with another embodiment of the present invention.

A method of detecting a flow parameter and a method of microfluidically dosing a fluid in accordance with the present invention shall now be described below with reference to FIGS. 8 and 9, respectively.

The inventive method 800 of detecting a flow parameter comprises selectively feeding 810 a first fluid to a first inlet of a channel by means of a micropump, and feeding a second fluid to a second inlet of the channel so as to form a fluid stream comprising the first and second fluids within the channel, and further to provide the fluid stream at an output of the channel, said channel having a cross-sectional dimensioning so as to configure, between a section of the channel that is filled with the first fluid and an adjacent section of the channel that is filled with the second fluid, a fluid boundary between the first and second fluids which extends over the entire channel cross-section, and the method 800 further comprises detecting 820, on the basis of a different physical property of the first fluid and the second fluid within the channel, a measurement value dependent on a current flow parameter of the first or second fluid.

The inventive method 900 for microfluidically dosing a fluid comprises detecting 910 a flow parameter, controlling 920 the first feed means to selectively feed in the first fluid and/or controlling the second feed means to selectively feed in the second fluid so as to obtain a predefined flow parameter of the first and second fluids within the channel; and separating 930 the first fluid from the fluid stream provided at the output of the channel so as to obtain an output-side fluid stream comprising the second fluid (F2).

Depending on specific implementation requirements, embodiments or functional elements such as, in particular, the controller 140 or other electronic elements or the procedural flows of the invention that have been illustrated may be implemented in hardware or in software. Said implementation may be performed using a digital storage medium, such as a floppy disk, a DVD, a Blu-ray disk, a CD, a ROM, a PROM, an EPROM, an EEPROM or a flash memory, a hard disk or any other magnetic or optical memory which has electronically readable control signals stored thereon that may cooperate, or cooperate, with a programmable computer system such that the respective method is performed. Therefore, the digital storage medium may be computer-readable. Thus, some embodiments in accordance with the invention comprise a data carrier having electronically readable control signals that are able to cooperate with a programmable computer system such that any of the methods described herein is performed.

Generally, embodiments of the present invention may be implemented as a computer program product having a program code, said program code being operative to perform any of the methods when the computer program product runs on a computer. The program code may also be stored on a machine-readable carrier, for example.

Other embodiments comprise the computer program for performing any of the methods described herein, said computer program being stored on a machine-readable carrier.

In other words, an embodiment of the inventive method therefore is a computer program which has a program code for performing any of the methods described herein, when the computer program runs on a computer. A further embodiment of the inventive methods therefore is a data carrier (or a digital storage medium or a computer-readable medium) having recorded thereon the computer program for performing any of the methods described herein.

According to one aspect, a microfluidic device 100, 200 for detecting a flow parameter comprises: a channel 104 configured within a base body 102, said channel 104 comprising a first inlet 106 for feeding a first fluid F1 and a second inlet 108 for feeding a second fluid F2 so as to form a fluid stream $F_{1-2}$ having the first and second fluids F1, F2 within the channel 104, and further comprising an output 112 for providing the fluid stream $F_{1-2}$ on the output side, and said channel 104 having a cross-sectional dimensioning for configuring within the channel 104, between a section of the channel 104 that is filled with the first fluid F1 and an adjacent section of the channel that is filled with the second fluid F2, a fluid interface between the first and second fluids F1, F2 that extends over the channel cross-section, a first feed means 114 comprising a micropump associated with the first inlet 106 for selectively feeding the first fluid F1 to the channel 104, a second feed means 116 associated with the second inlet 108 for feeding the second fluid F2 to the channel 104; and a detection means 118 for detecting, on the basis of a different physical property of the first fluid and the second fluid within the channel, a measurement value $S_{MEASURE}$ dependent on a current flow parameter of the first or second fluid.

The detection means 118 may further be configured to determine, on the basis of a different physical property of the first fluid F1 and the second fluid F2, a position or a change in the position of the fluid interface within the channel 104, the current flow parameter of the first or second fluid F1, F2 being determinable from the position or the change in position of the fluid interface.

According to a further aspect, the different physical property may be a different electrical conductivity, a different permittivity a different permeability, a different optical transparency or a different optical reflectivity of the first fluid F1 and of the second fluid F2.

According to a further aspect, the current flow parameter may indicate a flow velocity, a flow volume, a flow direction, a fluid propagation time and/or a filling level of the first or second fluid F1, F2 within the channel 104.

According to a further aspect, the detection means 118 of the microfluidic device may comprise a plurality of individual sensor elements along the fluid channel 104 that are configured to detect the different physical property of the first and second fluids F1, F2 in a spatially resolved manner at a plurality of positions along the channel 104 that are associated with the individual sensor elements.

According to a further aspect, the detection means 118 of the microfluidic device may be configured to capacitively detect the measurement value, and wherein two electrodes 118a, 118b that are insulated from each other and from the fluid stream $F_{1-2}$ are arranged on the base body 102, said two electrodes 118a, 118b being arranged opposite each other with regard to the channel 104, so that an electric field that may be generated between the two electrodes 118a, 118b exists both within that section of the channel 104 that is filled with the first fluid F1 and within that section of the channel 104 that is filled with the second fluid F2, so that a change in the position of the fluid stream $F_{1-2}$ leads to a proportional change in capacitance between the two electrodes 118a, 118b.

The first and second electrodes 118a, 118b may further each consist of a plurality of individual electrodes, so that a plurality of individual capacitances are formed between the first and second electrodes, said individual capacitances are detectable independently of one another.

The first and second electrodes 118a, 118b may further be arranged horizontally with regard to first and second main surfaces 102a, 102b of the base body 102 and at least partially cover the channel 104.

The first and second electrodes 118a, 118b may further be arranged vertically with regard to first and second main surfaces 102a, 102b of the base body 102 and extend along the channel in each case.

The first and second electrodes 118a, 118b may further each extend, at least in sections, along a curved external surface of the channel 104.

According to a further aspect, the detection means 118 of the microfluidic device may be configured to optically detect the position of the interface in the fluid stream $F_{1-2}$ within the channel 104, and wherein the channel is optically transparent at least on one of its sides.

According to a further aspect, the device further comprises: a fluid separation means 120 at the output 112 of the channel 104 for selectively separating the first fluid F1 from the fluid stream $F_{1\text{-}2}$ provided at the output 112 of the channel 104.

The fluid separation means 120 may further be arranged directly adjacent to the output 112 of the channel 104.

The fluid separation means 120 may further be fluidically coupled to the first inlet 106 so as to form a closed cycle for the first fluid F1 from the fluid separation means 120 to the first inlet 106 of the channel 104.

The fluid separation means 120 may further comprise a filter diaphragm repelling the second fluid which is arranged laterally to the output-side fluid stream within the chamber of the fluid separation means.

The fluid separation means 120 may further comprise, on the output side, a further detection means 128 configured to detect whether a quantity of the first fluid is present within the output-side fluid stream once it has passed the fluid separation means 120.

The further detection means 128 may be configured to quantitatively detect the quantity of the first fluid F1 present within the output-side fluid stream $F2_{OUT}$.

According to a further aspect, the device further comprises: a controller 140 configured to selectively control the first feed means 114 to feed in the first fluid F1 and/or the second feed means 116 to feed in the second fluid F2 so as to obtain a predefined flow parameter of the first and second fluids within the channel 104.

The controller 140 may further be configured to evaluate the measurement value $S_{MEASURE}$ detected by the detection means 118 and to determine the current flow parameter, said controller being further configured to control the first feed means 114 and/or the second feed means 116 on the basis of a deviation of the determined current flow parameter from the predefined flow parameter such as to obtain the predefined flow parameter of the first and/or second fluid within the channel.

According to a further aspect, the channel 104 of the device may be configured in a meander shape or helix shape within the base body 102.

According to a further aspect, the channel 104 of the device may have an elliptical or circular cross-sectional dimensioning, the small axis of the elliptical cross-section or the diameter of the circular cross-section being selected such that the position of the fluid interface is essentially determined by the interfacial tension of the second fluid F2, than the first fluid F1, and by the interfacial tension between the second fluid F2 and the material of the channel wall.

The channel 104 may have a rectangular cross-sectional dimensioning, the smaller side of the rectangular cross-sectional dimensioning being selected such that the position of the fluid interface is determined essentially by the interfacial tension of the second fluid F2 and by the interfacial tension between the second fluid F2 and the material of the channel wall.

According to a further aspect, at least one of the first and second inlets 106, 108 of the device may each have a disturbance detection means 130, 132 arranged thereat so as to detect accidental intrusion of the first fluid F1 into the second inlet 108 against the flow direction of the second fluid F2 or accidental intrusion of the second fluid F2 into the first inlet 106 against the flow direction of the first fluid F1.

According to a further aspect, the first fluid F1 may be gaseous and the second fluid F2 may be liquid.

The first fluid may further be liquid and the second fluid may be gaseous.

According to a further aspect, the first inlet 106 of the device may have a first reservoir 124 comprising the first fluid F1 associated with it, and the first feed means 114 may be configured to feed the first fluid F1 from the reservoir 124 to the first inlet 106.

According to a further aspect, the second inlet of the device may have a second reservoir 126 comprising the second fluid F2 associated with it, wherein the second feed means 116 may be configured to selectively feed the second fluid F2 from the second reservoir 126 to the second inlet 108.

According to a further aspect, the detection means of the device or a further detection means may be configured to detect the presence or passage of a fluid boundary at a predefined intermediate position within the channel 104 or at the channel output 112.

According to a further aspect, the second feed means 116 of the device associated with the second inlet 108 comprises a second micropump for selectively feeding the second fluid F2 to the channel 104.

The second micropump of the second feed means 114 may further be a peristaltic pump.

The first feed means 114 comprising the micropump and the second feed means 116 may further be arranged at the channel 104 on the input side, the second feed means 116 being arranged, in the flow direction, upstream from the first feed means 114, and the second feed means being arranged, as an opening within the channel for feeding the second fluid, wherein the first and the second feed means are configured to adjust the pressure P2 of the first fluid F1 in the first inlet 106 and the pressure P3 of the second fluid F2 in the second inlet 106 for injecting a quantity of the second fluid F2 into the channel 104 so as to form the interface between the first fluid F1 and the second fluid F2.

The first feed means 114 comprising the micropump and the second feed means 116 may further be arranged at the channel 104 on the input side, the second feed means 116 being arranged, in the flow direction, downstream from the first feed means 114, and the second feed means being arranged, as an opening within a narrowed channel section 116 for feeding the second fluid F2, wherein the first and the second feed means are configured to adjust the pressure P2 of the first fluid F1 in the first inlet 106 and the pressure P3 of the second fluid F2 in the second inlet 106 for injecting a quantity of the second fluid F2 into the channel 104 so as to form the interface between the first fluid F1 and the second fluid F2.

According to a further aspect, the micropump of the first feed means 114 of the device may be a peristaltic pump.

According to another aspect, a microfluidic dosing system 300, 400, 500 comprises: a microfluidic device 100, 200 for detecting a flow parameter comprises: a channel 104 configured within a base body 102, said channel 104 comprising a first inlet 106 for feeding a first fluid F1 and a second inlet 108 for feeding a second fluid F2 so as to form a fluid stream $F_{1\text{-}2}$ having the first and second fluids F1, F2 within the channel 104, and further comprising an output 112 for providing the fluid stream $F_{1\text{-}2}$ on the output side, and said channel 104 having a cross-sectional dimensioning for configuring within the channel 104, between a section of the channel 104 that is filled with the first fluid F1 and an adjacent section of the channel that is filled with the second fluid F2, a fluid interface between the first and second fluids F1, F2 that extends over the channel cross-section, a first feed means 114 comprising a micropump associated with the first inlet 106 for selectively feeding the first fluid F1 to the channel 104, a second feed means 116 associated with the second inlet 108 for feeding the second fluid F2 to the channel 104; and a detection means 118 for detecting, on the basis of a different physical property of the first fluid and the second fluid within the channel, a measurement value $S_{MEASURE}$ dependent on a current flow parameter of the first or second fluid; a controller 140 configured to selectively control the first feed means 114 to feed in the first fluid or the second feed means 116 to feed in the second fluid F2 so as to obtain a predefined flow parameter of the first or second fluid within the channel, and a fluid separation means 120 at the output 112 of the channel 104 for selectively separating the first fluid F1 from the fluid stream F$_{1-2}$ provided at the output 112 of the channel 104 so as to obtain, downstream from the fluid separation means, an output-side fluid stream F$_{OUT}$ comprising the fluid F2.

The controller 140 may further be configured to evaluate the measurement value detected by the detection means 118 and to determine the current flow parameter, said controller 140 being further configured to control the first feed means 114 or the second feed means 116 on the basis of a deviation of the determined current flow parameter from the predefined flow parameter such as to obtain the predefined flow parameter of the first and second fluids F1, F2 within the channel 104.

According to a further aspect, the controller 140 of the microfluidic dosing system may further be configured to control the first or second feed means 114, 116 to feed a predefined quantity of the first or second fluid into the channel on the input side.

According to a further aspect, the controller 140 of the microfluidic dosing system may further be configured to control the first feed means 114 to feed a predefined quantity of the first fluid F1 into a continuous stream of the second fluid F2 that is present at the channel 104 on the input side.

According to a further aspect, the controller 140 of the microfluidic dosing system may further be configured to control the first and second feed means 114, 116 such that the first and second fluids are fed into the channel 104 on the input side in a predefined ratio.

According to a further aspect, the controller 140 of the microfluidic dosing system may further be configured to control the first and second feed means 114, 116 such that a first quantity of the first fluid F1 and a second quantity of the second fluid F2 are alternately fed into the channel 104 on the input side in each case.

According to a further aspect, the detection means 118 or a further detection means 133, 134 of the microfluidic dosing system may be configured to detect the presence or passage of a fluid interface at the channel input 110, an intermediate position within the channel 104 or at the channel output 112.

According to a further aspect, the controller 140 of the microfluidic dosing system may further be configured to control the first and/or second feed means to stop feeding the second fluid F2 to the channel 104 on the input side when a fluid boundary comprising a transition from the first fluid to the second fluid is detected at an intermediate position within the channel 104 or at the channel output 112, so that a defined quantity of the second fluid F2 is present within the channel 104.

The controller 140 may further be configured to control the first feed means 114 to feed the first fluid F1 to the channel 104 so that the defined quantity of the second fluid F2 is provided, on the output side, at the channel output and/or in the flow direction downstream from the fluid separation means 120.

The controller 140 may further be configured to control the first or second feed means 114, 116 such that the first or second fluid F1, F2 are fed, on the input side, to the channel at a predefined flow velocity so as to obtain a predefined dosing volume, per time unit, of the first or second fluid F1, F2.

According to another aspect, a method of detecting a flow parameter, comprises: selectively feeding a first fluid to a first inlet of a channel by means of micropump, and feeding a second fluid to a second inlet of the channel so as to form a fluid stream comprising the first and second fluids within the channel, and to further provide the fluid stream at an output of the channel, said channel having a cross-sectional dimensioning for configuring, between a section of the channel that is filled with the first fluid and an adjacent section of the channel that is filled with the second fluid, a fluid boundary between the first and second fluids that extends over the entire channel cross-section, and detecting, on the basis of a different physical property of the first fluid and the second fluid within the channel, a measurement value dependent on a current flow parameter of the first or second fluid.

According to another aspect, a method of microfluidically dosing a fluid comprises: detecting a flow parameter, comprising: selectively feeding a first fluid to a first inlet of a channel by means of micropump, and feeding a second fluid to a second inlet of the channel so as to form a fluid stream comprising the first and second fluids within the channel, and to further provide the fluid stream at an output of the channel, said channel having a cross-sectional dimensioning for configuring, between a section of the channel that is filled with the first fluid and an adjacent section of the channel that is filled with the second fluid, a fluid boundary between the first and second fluids that extends over the entire channel cross-section, and detecting, on the basis of a different physical property of the first fluid and the second fluid within the channel, a measurement value dependent on a current flow parameter of the first or second fluid; controlling the first feed means to selectively feed the first fluid, and/or controlling the second feed means to selectively feed the second fluid so as to obtain a predefined flow parameter of the first and second fluids within the channel; and separating the first fluid from the fluid stream provided at the output of the channel so as to obtain an output-side fluid stream comprising the second fluid F2.

The method may further comprise: evaluating the measurement S$_{MEASURE}$ detected by the detection means, determining the current flow parameter, and controlling the first feed means and/or the second feed means on the basis of a deviation of the determined current flow parameter from the predefined flow parameter so as to obtain the predefined flow parameter of the first and second fluids within the channel.

According to a further aspect, the method may further comprise: detecting, on the basis of detecting a position of the interface within the channel, a quantity of the first fluid that has been fed into the channel, it being possible to associate a predefined quantity of the first fluid within the channel with the detected position.

According to a further aspect, the method may further comprise: detecting, on the basis of detecting positions of a plurality of interfaces within the channel, a quantity of the first fluid that has been fed into the channel, it being possible to associate a predefined quantity of the first fluid within the channel with the detected positions.

According to a further aspect, the method may further comprise: controlling the first or second feed means to feed a predefined quantity of the first or second fluid to the channel on the input side.

According to a further aspect, the method may further comprise: controlling the first feed means to feed a predefined quantity of the first fluid into a continuous stream of the second fluid that is present at the channel on the input side.

According to a further aspect, the method may further comprise: controlling the first and second feed means such that a first quantity of the first fluid and a second quantity of the second fluid are alternately fed into the channel on the input side in each case.

The method may further comprise: controlling the first and second feed means such that the first and second fluids are fed into the channel on the input side in a predefined ratio.

According to a further aspect, the method may further comprise: detecting the presence or passage of a fluid boundary at the channel or at an intermediate position in the channel output.

The method may further comprise: controlling the first and/or second controller to stop feeding the second fluid to the channel on the input side when a fluid interface comprising a transition from the first fluid to the second fluid is detected at an intermediate position within the channel or at the channel output, so that a predefined quantity of the second fluid is present within the channel.

The method may further comprise: controlling the first feed means to feed the first fluid to the channel on the input side at least for such time that the predefined quantity of the second fluid exits the channel output and/or the fluid separation means so as to provide, on the output side, the predefined quantity of the second fluid F2 as a dosing quantity.

According to a further aspect, the method may further comprise: controlling the first and/or second controller such that the first and/or second fluid are fed, on the input side, to the channel at a predefined flow velocity so as to continuously provide, on the output side, a predefined dosing quantity, per time unit, of the first or second fluid.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. A microfluidic device for detecting a flow parameter, comprising:
   a channel configured within a base body, said channel comprising a first inlet for feeding a first fluid and a second inlet for feeding a second fluid so as to form a fluid stream comprising the first and second fluids within the channel, and further comprising an output for providing the fluid stream on the output side, and
   said channel comprising a cross-sectional dimensioning for configuring within the channel, between a section of the channel that is filled with the first fluid and an adjacent section of the channel that is filled with the second fluid, a fluid interface between the first and second fluids that extends over the channel cross-section,
   a first feeder comprising a micro-membrane pump associated with the first net for selectively feeding the first fluid to the channel,
   a second feeder associated with the second inlet for feeding the second fluid to the channel; and
   a detector configured to detect, on the basis of a different physical property of the first fluid and the second fluid within the channel, a measurement value dependent on a current flow parameter of the first or second fluid;
   wherein the detector is configured to capacitively detect a position of the fluid interface within the channel, and wherein two electrodes are arranged on the base body, said two electrodes being arranged opposite to each other with regard to the channel, so that an electric field that may be generated between the two electrodes exists both within that section of the channel that is filled with the first fluid and within that section of the channel that is filled with the second fluid, so that a change in the position of the fluid stream leads to a proportional change in capacitance between the two electrodes; or
   wherein the detector is configured to resistively detect a position of the fluid interface within the channel, and wherein two electrodes are arranged on the base body, wherein a different electrical conductivity value exists within that section of the channel that is filled with the first fluid and within that section of the channel that is filled with the second fluid, so that a change in the position of the fluid stream leads to a proportional change in the electrical conductivity between the two electrodes; and wherein the detector comprises a plurality of individual sensor elements along the fluid channel that are configured to detect the different physical property of the first and second fluids in a spatially resolved manner at a plurality of positions along the channel that are associated with the individual sensor elements.

2. The device as claimed in claim 1, wherein the detector is configured to determine, on the basis of a different physical property of the first fluid and the second fluid, the position or a change in the position of the fluid interface within the channel, the current flow parameter of the first or second fluid being determinable from the position or the change in position of the fluid interface.

3. The device as claimed in claim 1, wherein the different physical property is a different electrical conductivity or a different permittivity of the first fluid and of the second fluid.

4. The device as claimed in claim 1, wherein the current flow parameter indicates a flow velocity, a flow volume, a flow direction, a fluid propagation time and/or a filling level of the first or second fluid within the channel.

5. The device as claimed in claim 1, wherein the first and second electrodes each comprise a plurality of individual electrodes, so that a plurality of individual capacitances are formed between the first and second electrodes, said individual capacitances are detectable independently of one another.

6. The device as claimed in claim 1, further comprising:
   a fluid separator at the output of the channel for selectively separating the first fluid from the fluid stream provided at the output of the channel.

7. The device as claimed in claim 1, further comprising:
   a controller configured to selectively control the first feeder to feed in the first fluid and/or the second feeder to feed in the second fluid so as to acquire a predefined flow parameter of the first and second fluids within the channel.

8. The device as claimed in claim 1, wherein at least one of the first and second inlets each comprise a disturbance detector arranged thereat so as to detect accidental intrusion of the first fluid into the second inlet against the flow direction of the second fluid or accidental intrusion of the second fluid into the first inlet against the flow direction of the first fluid.

9. The device as claimed in claim 1, wherein the first feeder comprising the micro-membrane pump and the second feeder are arranged at the channel on the input side, the second feeder being arranged, in the flow direction, upstream from the first feeder, and the second feeder being arranged, as an opening within the channel for feeding the second fluid, wherein the first and the second feeder are configured to adjust the pressure of the first fluid in the first inlet and the pressure of the second fluid in the second inlet for injecting a quantity of the second fluid into the channel based on a negative pressure as a result of a suction stroke of the micro-membrane pump of the first feeder so as to form the interface between the first fluid and the second fluid.

10. The device as claimed in claim 1, wherein the first feeder comprising the micro-membrane pump and the second feeder are arranged at the channel on the input side, the second feeder being arranged, in the flow direction, downstream from the first feeder, and the second feeder being arranged, as an opening within a narrowed channel section for feeding the second fluid, wherein the first and the second feeder are configured to adjust the pressure of the first fluid in the first inlet and the pressure of the second fluid in the second inlet for injecting a quantity of the second fluid into the channel based on a negative pressure as a result of a suction stroke of the micro-membrane pump of the first feeder so as to form the interface between the first fluid and the second fluid.

11. A microfluidic device configured to detect a flow parameter, comprising:
  a channel configured within a base body, said channel comprising a first inlet for feeding a first fluid and a second inlet for feeding a second fluid so as to form a fluid stream comprising the first and second fluids within the channel, and further comprising an output for providing the fluid stream on the output side, and
  said channel comprising a cross-sectional dimensioning for configuring within the channel, between a section of the channel that is filled with the first fluid and an adjacent section of the channel that is filled with the second fluid, a fluid interface between the first and second fluids that extends over the channel cross-section,
  a first feeder comprising a micro-membrane pump associated with the first inlet for selectively feeding the first fluid to the channel,
  a second feeder associated with the second inlet for feeding the second fluid to the channel; and
  a detector configured to detect, on the basis of a different physical property of the first fluid and the second fluid within the channel, a measurement value dependent on a current flow parameter of the first or second fluid;
  wherein the detector is configured to resistively detect a position of the fluid interface within the channel, and wherein two electrodes are arranged on the base body, wherein a different electrical conductivity value exists within that section of the channel that is filled with the first fluid and within that section of the channel that is filled with the second fluid, so that a change in the position of the fluid stream leads to a proportional change in the electrical conductivity between the two electrodes; and wherein the detector comprises a plurality of individual sensor elements along the fluid channel that are configured to detect the different physical property of the first and second fluids in a spatially resolved manner at a plurality of positions along the channel that are associated with the individual sensor elements.

12. A microfluidic device for detecting a flow parameter, comprising:
  a channel configured within a base body,
    said channel comprising a first inlet for feeding a first fluid and a second inlet for feeding a second fluid so as to form a fluid stream comprising the first and second fluids within the channel, and further comprising an output for providing the fluid stream on the output side, and
    said channel comprising a cross-sectional dimensioning for configuring within the channel, between a section of the channel that is filled with the first fluid and an adjacent section of the channel that is filled with the second fluid, a fluid interface between the first and second fluids that extends over the channel cross-section,
  a first feeder comprising a micro-membrane pump associated with the first inlet for selectively feeding the first fluid to the channel,
  a second feeder associated with the second inlet for feeding the second fluid to the channel; and
  a detector configured to detect, on the basis of a different physical property of the first fluid and the second fluid within the channel, a measurement value dependent on a current flow parameter of the first or second fluid;
  wherein the detector comprises a plurality of individual sensor elements along the fluid channel that are configured to detect the different physical property of the first and second fluids in a spatially resolved manner at a plurality of positions along the channel that are associated with the individual sensor elements.

13. A microfluidic device for detecting a flow parameter, comprising:
  a channel configured within a base body, said channel comprising a first inlet for feeding a first fluid and a second inlet for feeding a second fluid so as to form a fluid stream comprising the first and second fluids within the channel, and further comprising an output for providing the fluid stream on the output side, and
  said channel comprising a cross-sectional dimensioning for configuring within the channel, between a section of the channel that is filled with the first fluid and an adjacent section of the channel that is filled with the second fluid, a fluid interface between the first and second fluids that extends over the channel cross-section,
  a first feeder comprising a micro-membrane pump associated with the first inlet for selectively feeding the first fluid to the channel,
  a second feeder associated with the second inlet for feeding the second fluid to the channel; and
  a detector configured to detect, on the basis of a different physical property of the first fluid and the second fluid within the channel, a measurement value dependent on a current flow parameter of the first or second fluid;
  wherein at least one of the first and second inlets each comprise a disturbance detector arranged thereat so as to detect accidental intrusion of the first fluid into the second inlet against the flow direction of the second fluid or accidental intrusion of the second fluid into the first inlet against the flow direction of the first fluid; and wherein the detector comprises a plurality of individual sensor elements along the fluid channel that are configured to detect the different physical property of the first and second fluids in a spatially resolved manner at a plurality of positions along the channel that are associated with the individual sensor elements.

14. The device as claimed in claim 1, wherein the micro-membrane pump is arranged on the base body.

15. The device as claimed in claim 1, wherein the detector is arranged on the base body.

16. The device as claimed in claim 1, wherein the micro-membrane pump, the second feeder and the detector are arranged on the base body.

17. The device as claimed in claim 1, wherein the second feeder comprises a further micro-membrane pump.

18. The device as claimed in claim 11, further comprising:
  a controller configured to selectively control the first feeder to feed in the first fluid or the second feeder to feed in the second fluid so as to acquire a predefined flow parameter of the first or second fluid within the channel, and a fluid separator at the output of the channel for selectively separating the first fluid from the fluid stream provided at the output of the channel so as to acquire, downstream from the fluid separator, an output-side fluid stream comprising the fluid.

\* \* \* \* \*